US010844374B2

(12) United States Patent
Yokota et al.

(10) Patent No.: US 10,844,374 B2
(45) Date of Patent: Nov. 24, 2020

(54) CHIMERIC SINGLE-STRANDED ANTISENSE POLYNUCLEOTIDES AND DOUBLE-STRANDED ANTISENSE AGENT

(71) Applicant: National University Corporation Tokyo Medical and Dental University, Tokyo (JP)

(72) Inventors: Takanori Yokota, Tokyo (JP); Kazutaka Nishina, Tokyo (JP); Hidehiro Mizusawa, Tokyo (JP); Takeshi Wada, Tokyo (JP)

(73) Assignee: National University Corporation Tokyo Medical and Dental University, Tokyo (JP)

( * ) Notice: Subject to any disclaimer, the term of this patent is extended or adjusted under 35 U.S.C. 154(b) by 0 days.

(21) Appl. No.: 15/616,120

(22) Filed: Jun. 7, 2017

(65) Prior Publication Data
US 2017/0275627 A1  Sep. 28, 2017

Related U.S. Application Data

(62) Division of application No. 14/771,252, filed as application No. PCT/JP2014/001159 on Mar. 3, 2014, now abandoned.

(60) Provisional application No. 61/909,179, filed on Nov. 26, 2013, provisional application No. 61/806,887, filed on Mar. 31, 2013, provisional application No. 61/771,115, filed on Mar. 1, 2013.

(51) Int. Cl.
| | |
|---|---|
| *C12N 15/11* | (2006.01) |
| *C12N 15/113* | (2010.01) |
| *A61K 31/7088* | (2006.01) |
| *A61K 31/712* | (2006.01) |
| *A61K 31/7125* | (2006.01) |
| *A61K 31/713* | (2006.01) |

(52) U.S. Cl.
CPC ........ *C12N 15/113* (2013.01); *A61K 31/7088* (2013.01); *A61K 31/712* (2013.01); *A61K 31/713* (2013.01); *A61K 31/7125* (2013.01); *C12N 15/111* (2013.01); *C12N 2310/11* (2013.01); *C12N 2310/14* (2013.01); *C12N 2310/315* (2013.01); *C12N 2310/3231* (2013.01); *C12N 2310/341* (2013.01); *C12N 2310/53* (2013.01); *C12N 2310/533* (2013.01)

(58) Field of Classification Search
CPC . C12N 15/111; C12N 15/113; C12N 2310/11; C12N 2310/14; C12N 2310/341; C12N 2310/346; C12N 2310/321
See application file for complete search history.

(56) References Cited

U.S. PATENT DOCUMENTS

| | | | |
|---|---|---|---|
| 6,043,060 A | 3/2000 | Imanishi | |
| 2002/0068708 A1 | 6/2002 | Wengel et al. | |
| 2003/0105309 A1 | 6/2003 | Imanishi et al. | |
| 2005/0014712 A1 | 1/2005 | Hansen et al. | |
| 2005/0245474 A1* | 11/2005 | Baker | C12N 15/111 514/44 A |
| 2006/0134787 A1* | 6/2006 | Zamore | C12N 15/111 435/455 |
| 2007/0123484 A1* | 5/2007 | Bhat | C07H 21/02 514/44 A |
| 2007/0167387 A1 | 7/2007 | Imanishi et al. | |
| 2009/0306178 A1* | 12/2009 | Bhat | A61K 31/7125 514/44 A |
| 2010/0197762 A1 | 8/2010 | Swayze | |
| 2013/0184324 A1* | 7/2013 | Fitzgerald | A61K 31/713 514/44 A |
| 2015/0184153 A1* | 7/2015 | Freier | C12Y 301/03016 514/44 A |

(Continued)

FOREIGN PATENT DOCUMENTS

| | | |
|---|---|---|
| JP | 10-195098 A | 7/1998 |
| JP | 10-304889 A | 11/1998 |
| JP | 2002-521310 A | 7/2002 |

(Continued)

OTHER PUBLICATIONS

NCBI Reference sequence Accession NM_000314, version NM_000314.1, *Homo sapiens* phosphatase and tensin homolog (mutated in multiple advanced cancers 1) (PTEN), mRNA, accessed and retrieved from www.ncbi.nlm.nih.gov on Jan. 29, 2019. Last modified on Oct. 4, 2003. (Year: 2003).*

(Continued)

*Primary Examiner* — Dana H Shin
(74) *Attorney, Agent, or Firm* — Foley & Lardner LLP

(57) ABSTRACT

Chimeric single-stranded polynucleotides and double-stranded antisense agents useful for modifying the expression of a target gene by means of an antisense effect are disclosed. The chimeric single-stranded antisense polynucleotide and double-stranded antisense agents comprise a central nucleotide region flanked by a first 5'-wing region and a first 3'-wing region of modified nucleotides, which are themselves flanked by a second 5'-wing region and/or a second 3'-wing region of nucleotides that have a low affinity for proteins and/or that have higher resistance to DNase or RNase than a natural DNA or RNA and are missing in a cell when the chimeric polynucleotide delivered. The double-stranded antisense agent further comprises a complementary strand annealed to the antisense strand. The polynucleotide can be used to modify RNA transcription levels, miRNA activity, or protein levels in cells.

20 Claims, 18 Drawing Sheets
Specification includes a Sequence Listing.

(56) References Cited

U.S. PATENT DOCUMENTS

2015/0275208 A1  10/2015  Oestergaard et al.

FOREIGN PATENT DOCUMENTS

| WO | WO 99/14226 | A2 | 3/1999 |
| WO | WO 03/011887 | A2 | 2/2003 |
| WO | WO 2005/021570 | A1 | 3/2005 |
| WO | WO 2007/131238 | A2 | 11/2007 |
| WO | WO 2007/143315 | A2 | 12/2007 |
| WO | WO 2008/029619 | A1 | 3/2008 |
| WO | WO 2008/043753 | A2 | 4/2008 |
| WO | WO 2009/067243 | A2 | 5/2009 |
| WO | WO 2012/109395 | A1 | 8/2012 |
| WO | WO 2012/174476 | A2 | 12/2012 |
| WO | WO 2013/003808 | A1 | 1/2013 |

OTHER PUBLICATIONS

Lamberton et al., Varying the nucleic acid composition of siRNA molecules dramatically varies the duration and degree of gene silencing, Molecular Biotechnology, vol. 24, pp. 111-119. (Year: 2003).*

Lendvai et al., "Biodistribution of $^{68}$Ga-Labeled LNA-DNA Mixmer Antisense Oligonucleotides for Rat Chromogranin-A," Oligonucleotides, 2008, 18:33-49.

Crooke et al., "Clinical pharmacological properties of mipomersen (Kynamro), a second generation antisense inhibitor of apolipoprotein B," British Journal of Clinical Pharmacology, Sep. 26, 2012, 76(2):269-276.

International Search Report dated Mar. 25, 2014, in PCT/JP2014/001159.

Jepsen et al., Downregulation of p21(WAF1/CIP1) and estrogen receptor alpha in MCF-7 cells by antisense oligonucleotides containing locked nucleic acid (LNA), 2004, 14:147-156.

Nishina et al., "Efficient In Vivo Delivery of siRNA to the Liver by Conjugation of α-Tocopherol," Molecular Therapy, Apr. 2008, 16(4):734-740.

Peer et al., "Systemic Leukocyte-Directed siRNA Delivery Revealing Cyclin D1 as an Anti-Inflammatory Target," Science, Feb. 1, 2008, 319:627-630.

Soutschek et al., "Therapeutic silencing of an endogenous gene by systemic administration of modified siRNAs," Nature, Nov. 11, 2004, 432:173-178.

Stenvang et al., "Inhibition of microRNA function by antimiR oligonucleotides," Silence, 2012, 3:1, 17 pages.

Straarup et al., "Short locked nucleic acid antisense oligonucleotides potently reduce apolipopritein B mRNA and serum cholesterol in mice and non-human primates," Nucleic Acids Research, Jul. 8, 2010, 38(20):7100-7111.

Supplementary European Search Report dated Aug. 22, 2016, in EP 14757511.2.

Yamamoto et al., "Superior Silencing by 2',4'-BNA$^{NC}$-Based Short Antisense Oligonucleotides Compared to 2',4'-BNA/LNA-Based Apolipoprotein B Antisense Inhibitors," Journal of Nucleic Acids, 2012, Article ID 707323, 7 pages.

* cited by examiner

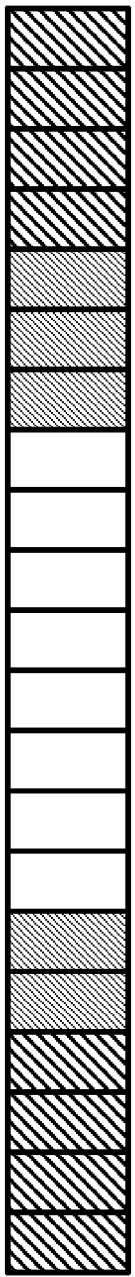
FIG. 6A
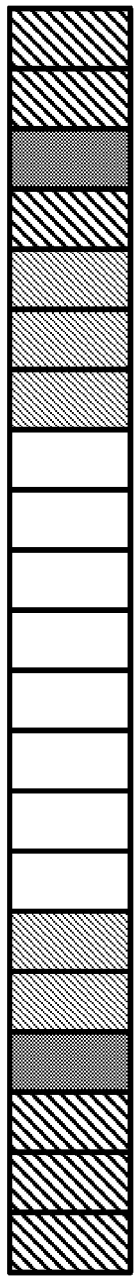
FIG. 6B
FIG. 6C
FIG. 6D
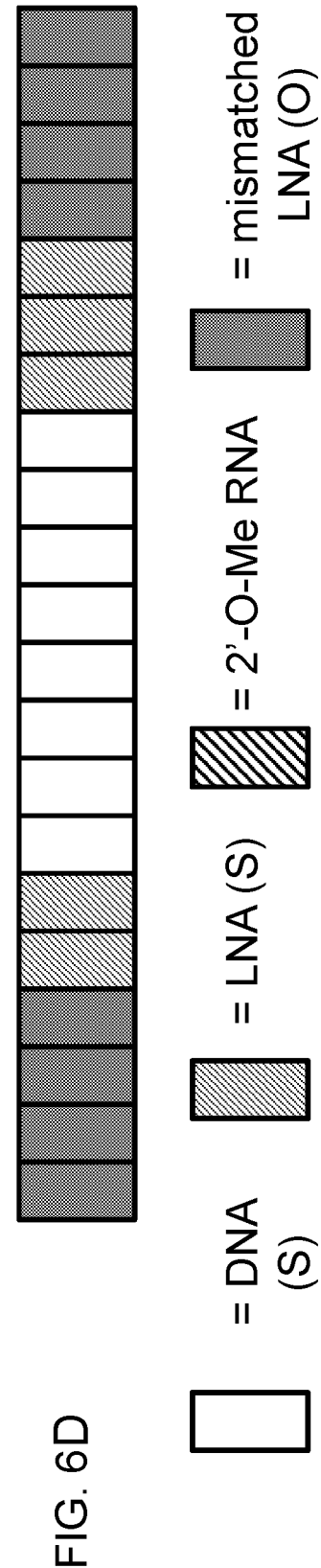

Fig. 8A

| | | |
|---|---|---|
| 20mer gapmer | *TCCAGC*attggtat*TCAGTG* (SEQ ID NO:11) | (6-8-6) LNA gapmer |
| 20mer chimera 5'/3' wing | TCCAGC*attggtatTCAGTG* (SEQ ID NO:12) | (4-2-8-3-3) winged gapmer |
| 20mer chimera 3' wing | GC*attggtatTCAGTGTGAT* (SEQ ID NO:13) | (2-8-3-7) winged gapmer |
| 20mer chimera 5' wing | AAGTCCAG*Cattggtat*TCA (SEQ ID NO:14) | (7-2-8-3) winged gapmer |
| 13mer gapmer | GC*attggtatTCA* (SEQ ID NO:15) | (2-8-3) LNA gapmer |

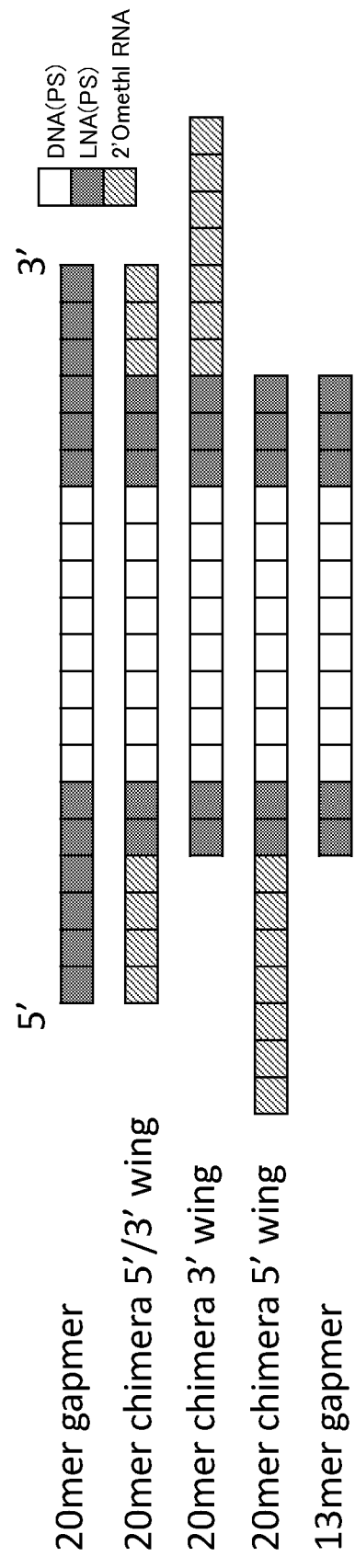

20mer gapmer
20mer chimera 5'/3' wing
20mer chimera 3' wing
20mer chimera 5' wing
13mer gapmer Linkages between DNA and DNA, DNA and LNA and LNA and LNA are phosphorothioate linkages.

Fig. 9

| ASO Name | Sequence | |
|---|---|---|
| 20mer-1 ApoB1 ASO | 5'-TsCsAsGscsaststsgsgstsaststsCsAsGsTsG-3' | (16) |
| 20mer-4 ApoB1 ASO | 5'-uscscsasGsCsaststsgsgstsastsTsCsAsgsusg-3' | (6) |
| 20mer-5 ApoB1 ASO | 5'-uccaGsCsaststsgsgstsastsTsCsAgug-3' | (7) |
| 13mer ApoB1 ASO | 5'-GsCsaststsgsgstsastsTsCsA-3' | (8) |

(Number in bracket after the sequence represents SEQ ID.)
Capitalized : LNA　Uncapitalized : DNA　Underlined : 2'-O-Me RNA　s : phosphorothioate

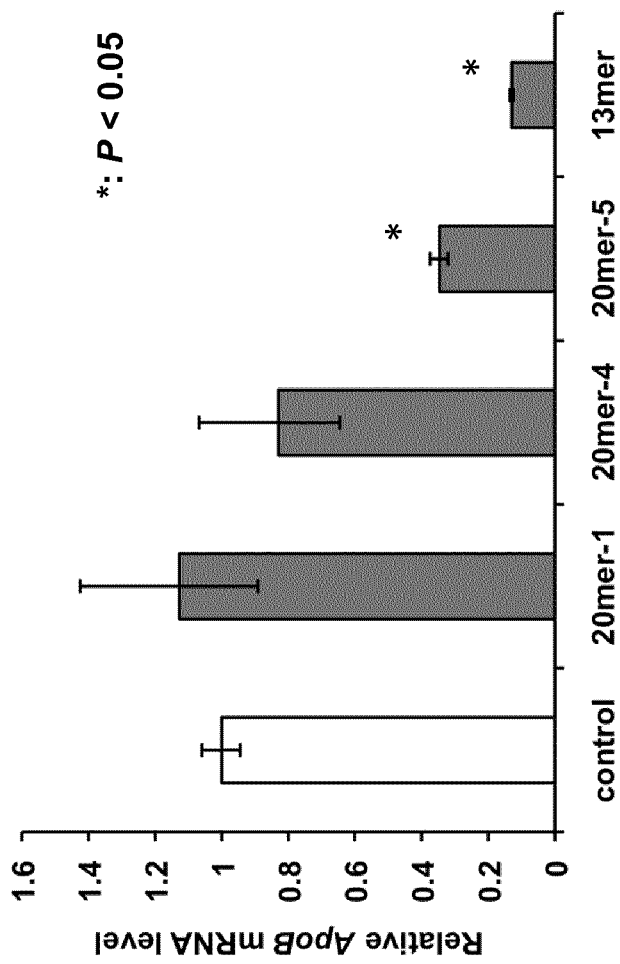

ASO Name | Sequence
20mer-1 ApoB1 ASO | 5'-TsCsCsAsGscsastStsgsgstsastsCsAsGsTsG-3' (16)
20mer-4 ApoB1 ASO | 5'-uscsCsasGsCsastStsgsgstsastsTsCsAsgsusg-3' (6)
20mer-5 ApoB1 ASO | 5'-uccaGsCsastStsgsgstsastsTsCsAgug-3' (7)
13mer ApoB1 ASO | 5'-GsCsastStsgsgstsastsTsCsA-3' (8)

(Number in bracket after the sequence represents SEQ ID NO.)

cRNA Name | Sequence
20mer Toc-ApoB1 cRNA | 5'-Toc-csascsusgsAAUACCAAUGscsusgsgsa-3' (17)
13mer Toc-ApoB1 cRNA | 5'-Toc-usgsasAUACCAAUsgsc-3' (18)

Capitalized : LNA
Uncapitalized : DNA
Underlined : 2'-O-Me RNA
s : phosphorothioate
Bold Capitalized: RNA

SEQUENCE LISTING

```
<160> NUMBER OF SEQ ID NOS: 19

<210> SEQ ID NO 1
<211> LENGTH: 13
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6),
      (6)..(7)
<223> OTHER INFORMATION: Phosphorothioate linkage
<220> FEATURE:
<221> NAME/KEY: misc_feature
<222> LOCATION: (7)..(8), (8)..(9), (9)..(10), (10)..(11), (11)..(12),
      (12)..(13)
<223> OTHER INFORMATION: Phosphorothioate linkage
<220> FEATURE:
<221> NAME/KEY: misc_feature
<222> LOCATION: (1)..(1), (2)..(2), (11)..(11), (12)..(12), (13)..(13)
<223> OTHER INFORMATION: LNA

<400> SEQUENCE: 1
gcattggtat tca                                                      13

<210> SEQ ID NO 2
<211> LENGTH: 17
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (5)..(6), (6)..(7), (7)..(8), (8)..(9), (9)..(10),
      (10)..(11)
<223> OTHER INFORMATION: Phosphorothioate linkage
<220> FEATURE:
<221> NAME/KEY: misc_feature
<222> LOCATION: (11)..(12), (12)..(13), (13)..(14), (14)..(15),
      (15)..(16)
```

```
<223> OTHER INFORMATION: Phosphorothioate linkage
<220> FEATURE:
<221> NAME/KEY: misc_feature
<222> LOCATION: (16)..(17)
<223> OTHER INFORMATION: Phosphorothioate linkage
<220> FEATURE:
<221> NAME/KEY: misc_feature
<222> LOCATION: (5)..(5), (6)..(6), (15)..(15), (16)..(16), (17)..(17)
<223> OTHER INFORMATION: LNA
<220> FEATURE:
<221> NAME/KEY: misc_feature
<222> LOCATION: (1)..(1), (2)..(2), (3)..(3), (4)..(4)
<223> OTHER INFORMATION: 2-o-Me

<400> SEQUENCE: 2
uccagcattg gtattca                                                    17

<210> SEQ ID NO 3
<211> LENGTH: 20
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (8)..(9), (9)..(10), (10)..(11), (11)..(12), (12)..(13)
<223> OTHER INFORMATION: Phosphorothioate linkage
<220> FEATURE:
<221> NAME/KEY: misc_feature
<222> LOCATION: (13)..(14), (14)..(15), (15)..(16), (16)..(17),
      (17)..(18)
<223> OTHER INFORMATION: Phosphorothioate linkage
<220> FEATURE:
<221> NAME/KEY: misc_feature
<222> LOCATION: (18)..(19), (19)..(20)
<223> OTHER INFORMATION: Phosphorothioate linkage
<220> FEATURE:
<221> NAME/KEY: misc_feature
<222> LOCATION: (8)..(8), (9)..(9), (18)..(18), (19)..(19), (20)..(20)
<223> OTHER INFORMATION: LNA
<220> FEATURE:
<221> NAME/KEY: misc_feature
<222> LOCATION: (1)..(1), (2)..(2), (3)..(3), (4)..(4), (5)..(5),
      (6)..(6), (7)..(7)
<223> OTHER INFORMATION: 2-o-Me

<400> SEQUENCE: 3
aaguccagca ttggtattca                                                 20

<210> SEQ ID NO 4
<211> LENGTH: 20
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (1)..(2), (2)..(3), (3)..(4), (4)..(5), (5)..(6),
      (6)..(7)
<223> OTHER INFORMATION: Phosphorothioate linkage
<220> FEATURE:
<221> NAME/KEY: misc_feature
<222> LOCATION: (7)..(8), (8)..(9), (9)..(10), (10)..(11), (11)..(12),
      (12)..(13)
<223> OTHER INFORMATION: Phosphorothioate linkage
<220> FEATURE:
<221> NAME/KEY: misc_feature
<222> LOCATION: (13)..(14), (14)..(15), (15)..(16), (16)..(17),
      (17)..(18)
<223> OTHER INFORMATION: Phosphorothioate linkage
<220> FEATURE:
```

<221> NAME/KEY: misc_feature
<222> LOCATION: (18)..(19), (19)..(20)
<223> OTHER INFORMATION: Phosphorothioate linkage
<220> FEATURE:
<221> NAME/KEY: misc_feature
<222> LOCATION: (8)..(8), (9)..(9), (18)..(18), (19)..(19), (20)..(20)
<223> OTHER INFORMATION: LNA
<220> FEATURE:
<221> NAME/KEY: misc_feature
<222> LOCATION: (1)..(1), (2)..(2), (3)..(3), (4)..(4), (5)..(5),
      (6)..(6), (7)..(7)
<223> OTHER INFORMATION: 2-o-Me

<400> SEQUENCE: 4
aaguccagca ttggtattca                                               20

<210> SEQ ID NO 5
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6),
      (6)..(7)
<223> OTHER INFORMATION: Phosphorothioate linkage
<220> FEATURE:
<221> NAME/KEY: misc_feature
<222> LOCATION: (7)..(8), (8)..(9), (9)..(10), (10)..(11), (11)..(12),
      (12)..(13)
<223> OTHER INFORMATION: Phosphorothioate linkage
<220> FEATURE:
<221> NAME/KEY: misc_feature
<222> LOCATION: (13)..(14), (14)..(15), (15)..(16), (16)..(17),
      (17)..(18)
<223> OTHER INFORMATION: Phosphorothioate linkage
<220> FEATURE:
<221> NAME/KEY: misc_feature
<222> LOCATION: (18)..(19), (19)..(20)
<223> OTHER INFORMATION: Phosphorothioate linkage
<220> FEATURE:
<221> NAME/KEY: misc_feature
<222> LOCATION: (1)..(1), (2)..(2), (3)..(3), (4)..(4), (5)..(5),
      (6)..(6)
<223> OTHER INFORMATION: LNA
<220> FEATURE:
<221> NAME/KEY: misc_feature
<222> LOCATION: (15)..(15), (16)..(16), (17)..(17), (18)..(18),
      (19)..(19)
<223> OTHER INFORMATION: LNA
<220> FEATURE:
<221> NAME/KEY: misc_feature
<222> LOCATION: (20)..(20)
<223> OTHER INFORMATION: LNA

<400> SEQUENCE: 5
tccagcattg gtattcagtg                                               20

<210> SEQ ID NO 6
<211> LENGTH: 20
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (1)..(2), (2)..(3), (3)..(4), (4)..(5), (5)..(6),
      (6)..(7)
<223> OTHER INFORMATION: Phosphorothioate linkage
<220> FEATURE:
<221> NAME/KEY: misc_feature
<222> LOCATION: (7)..(8), (8)..(9), (9)..(10), (10)..(11), (11)..(12),

```
          (12)..(13)
<223> OTHER INFORMATION: Phosphorothioate linkage
<220> FEATURE:
<221> NAME/KEY: misc_feature
<222> LOCATION: (13)..(14), (14)..(15), (15)..(16), (16)..(17),
      (17)..(18)
<223> OTHER INFORMATION: Phosphorothioate linkage
<220> FEATURE:
<221> NAME/KEY: misc_feature
<222> LOCATION: (18)..(19), (19)..(20)
<223> OTHER INFORMATION: Phosphorothioate linkage
<220> FEATURE:
<221> NAME/KEY: misc_feature
<222> LOCATION: (5)..(5), (6)..(6), (15)..(15), (16)..(16), (17)..(17),
<223> OTHER INFORMATION: LNA
<220> FEATURE:
<221> NAME/KEY: misc_feature
<222> LOCATION: (1)..(1), (2)..(2), (3)..(3), (4)..(4), (18)..(18),
      (19)..(19)
<223> OTHER INFORMATION: 2-o-Me
<220> FEATURE:
<221> NAME/KEY: misc_feature
<222> LOCATION: (20)..(20)
<223> OTHER INFORMATION: 2-o-Me

<400> SEQUENCE: 6
uccagcattg gtattcagug                                             20

<210> SEQ ID NO 7
<211> LENGTH: 20
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (5)..(6), (6)..(7), (7)..(8), (8)..(9), (9)..(10),
      (10)..(11)
<223> OTHER INFORMATION: Phosphorothioate linkage
<220> FEATURE:
<221> NAME/KEY: misc_feature
<222> LOCATION: (11)..(12), (12)..(13), (13)..(14), (14)..(15),
      (15)..(16)
<223> OTHER INFORMATION: Phosphorothioate linkage
<220> FEATURE:
<221> NAME/KEY: misc_feature
<222> LOCATION: (16)..(17)
<223> OTHER INFORMATION: Phosphorothioate linkage
<220> FEATURE:
<221> NAME/KEY: misc_feature
<222> LOCATION: (5)..(5), (6)..(6), (15)..(15), (16)..(16), (17)..(17),
<223> OTHER INFORMATION: LNA
<220> FEATURE:
<221> NAME/KEY: misc_feature
<222> LOCATION: (1)..(1), (2)..(2), (3)..(3), (4)..(4), (18)..(18),
      (19)..(19)
<223> OTHER INFORMATION: 2-o-Me
<220> FEATURE:
<221> NAME/KEY: misc_feature
<222> LOCATION: (20)..(20)
<223> OTHER INFORMATION: 2-o-Me

<400> SEQUENCE: 7
uccagcattg gtattcagug                                             20

<210> SEQ ID NO 8
<211> LENGTH: 13
<212> TYPE: DNA
<213> ORGANISM: Artificial
<220> FEATURE:
<223> OTHER INFORMATION: Synthetic
<220> FEATURE:
<221> NAME/KEY: misc_feature
```

```
<222> LOCATION: (1)..(2), (2)..(3), (3)..(4), (4)..(5), (5)..(6),
      (6)..(7)
<223> OTHER INFORMATION: Phosphorothioate linkage
<220> FEATURE:
<221> NAME/KEY: misc_feature
<222> LOCATION: (7)..(8), (8)..(9), (9)..(10), (10)..(11), (11)..(12),
      (12)..(13)
<223> OTHER INFORMATION: Phosphorothioate linkage
<220> FEATURE:
<221> NAME/KEY: misc_feature
<222> LOCATION: (1)..(1), (2)..(2), (11)..(11), (12)..(12), (13)..(13)
<223> OTHER INFORMATION: LNA

<400> SEQUENCE: 8
gcattggtat tca                                                      13

<210> SEQ ID NO 9
<211> LENGTH: 20
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6),
      (15)..(16)
<223> OTHER INFORMATION: Phosphorothioate linkage
<220> FEATURE:
<221> NAME/KEY: misc_feature
<222> LOCATION: (16)..(17), (17)..(18), (18)..(19), (19)..(20)
<223> OTHER INFORMATION: Phosphorothioate linkage
<220> FEATURE:
<221> NAME/KEY: misc_feature
<222> LOCATION: (1)..(1), (2)..(2), (3)..(3), (4)..(4), (5)..(5),
      (16)..(16)
<223> OTHER INFORMATION: 2-O-Me
<220> FEATURE:
<221> NAME/KEY: misc_feature
<222> LOCATION: (17)..(17), (18)..(18), (19)..(19), (20)..(20)
<223> OTHER INFORMATION: 2-O-Me

<400> SEQUENCE: 9
cacugaauac caaugcugga                                               20

<210> SEQ ID NO 10
<211> LENGTH: 13
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (11)..(12), (12)..(13)
<223> OTHER INFORMATION: Phosphorothioate linkage
<220> FEATURE:
<221> NAME/KEY: misc_feature
<222> LOCATION: (1)..(1), (2)..(2), (3)..(3), (12)..(12), (13)..(13)
<223> OTHER INFORMATION: 2-O-Me

<400> SEQUENCE: 10
ugaauaccaa ugc                                                      13

<210> SEQ ID NO 11
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6),
      (6)..(7)
<223> OTHER INFORMATION: Phosphorothioate linkage
```

```
<220> FEATURE:
<221> NAME/KEY: misc_feature
<222> LOCATION: (7)..(8), (8)..(9), (9)..(10), (10)..(11), (11)..(12),
      (12)..(13)
<223> OTHER INFORMATION: Phosphorothioate linkage
<220> FEATURE:
<221> NAME/KEY: misc_feature
<222> LOCATION: (13)..(14), (14)..(15), (15)..(16), (16)..(17),
      (17)..(18)
<223> OTHER INFORMATION: Phosphorothioate linkage
<220> FEATURE:
<221> NAME/KEY: misc_feature
<222> LOCATION: (18)..(19), (19)..(20)
<223> OTHER INFORMATION: Phosphorothioate linkage
<220> FEATURE:
<221> NAME/KEY: misc_feature
<222> LOCATION: (1)..(1), (2)..(2), (3)..(3), (4)..(4), (5)..(5),
      (6)..(6)
<223> OTHER INFORMATION: LNA
<220> FEATURE:
<221> NAME/KEY: misc_feature
<222> LOCATION: (15)..(15), (16)..(16), (17)..(17), (18)..(18),
      (19)..(19)
<223> OTHER INFORMATION: LNA
<220> FEATURE:
<221> NAME/KEY: misc_feature
<222> LOCATION: (20)..(20)
<223> OTHER INFORMATION: LNA

<400> SEQUENCE: 11
tccagcattg gtattcagtg                                                  20

<210> SEQ ID NO 12
<211> LENGTH: 20
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (5)..(6), (6)..(7), (7)..(8), (8)..(9), (9)..(10),
      (10)..(11)
<223> OTHER INFORMATION: Phosphorothioate linkage
<220> FEATURE:
<221> NAME/KEY: misc_feature
<222> LOCATION: (11)..(12), (12)..(13), (13)..(14), (14)..(15),
      (15)..(16)
<223> OTHER INFORMATION: Phosphorothioate linkage
<220> FEATURE:
<221> NAME/KEY: misc_feature
<222> LOCATION: (16)..(17)
<223> OTHER INFORMATION: Phosphorothioate linkage
<220> FEATURE:
<221> NAME/KEY: misc_feature
<222> LOCATION: (5)..(5), (6)..(6), (15)..(15), (16)..(16), (17)..(17)
<223> OTHER INFORMATION: LNA
<220> FEATURE:
<221> NAME/KEY: misc_feature
<222> LOCATION: (1)..(1), (2)..(2), (3)..(3), (4)..(4), (18)..(18),
      (19)..(19)
<223> OTHER INFORMATION: 2-o-Me
<220> FEATURE:
<221> NAME/KEY: misc_feature
<222> LOCATION: (20)..(20)
<223> OTHER INFORMATION: 2-o-Me

<400> SEQUENCE: 12
tccagcattg gtattcagtg                                                  20

<210> SEQ ID NO 13
<211> LENGTH: 20
<212> TYPE: DNA
<213> ORGANISM: Artificial
```

```
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (1)..(2), (2)..(3), (3)..(4), (4)..(5), (5)..(6),
      (6)..(7)
<223> OTHER INFORMATION: Phosphorothioate linkage
<220> FEATURE:
<221> NAME/KEY: misc_feature
<222> LOCATION: (7)..(8), (8)..(9), (9)..(10), (10)..(11), (11)..(12),
      (12)..(13)
<223> OTHER INFORMATION: Phosphorothioate linkage
<220> FEATURE:
<221> NAME/KEY: misc_feature
<222> LOCATION: (1)..(1), (2)..(2), (11)..(11), (12)..(12), (13)..(13)
<223> OTHER INFORMATION: LNA
<220> FEATURE:
<221> NAME/KEY: misc_feature
<222> LOCATION: (14)..(14), (15)..(15), (16)..(16), (17)..(17),
      (18)..(18)
<223> OTHER INFORMATION: 2-o-Me
<220> FEATURE:
<221> NAME/KEY: misc_feature
<222> LOCATION: (19)..(19), (20)..(20)
<223> OTHER INFORMATION: 2-o-Me

<400> SEQUENCE: 13
gcattggtat tcagtgtgat                                              20

<210> SEQ ID NO 14
<211> LENGTH: 20
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (8)..(9), (9)..(10), (10)..(11), (11)..(12), (12)..(13),
      (13)..(14)
<223> OTHER INFORMATION: Phosphorothioate linkage
<220> FEATURE:
<221> NAME/KEY: misc_feature
<222> LOCATION: (14)..(15), (15)..(16), (16)..(17), (17)..(18),
      (18)..(19)
<223> OTHER INFORMATION: Phosphorothioate linkage
<220> FEATURE:
<221> NAME/KEY: misc_feature
<222> LOCATION: (19)..(20)
<223> OTHER INFORMATION: Phosphorothioate linkage
<220> FEATURE:
<221> NAME/KEY: misc_feature
<222> LOCATION: (8)..(8), (9)..(9), (18)..(18), (19)..(19), (20)..(20)
<223> OTHER INFORMATION: LNA
<220> FEATURE:
<221> NAME/KEY: misc_feature
<222> LOCATION: (1)..(1), (2)..(2), (3)..(3), (4)..(4), (5)..(5),
      (6)..(6), (7)..(7)
<223> OTHER INFORMATION: 2-o-Me

<400> SEQUENCE: 14
aagtccagca ttggtattca                                              20

<210> SEQ ID NO 15
<211> LENGTH: 13
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6),
```

```
        (6)..(7)
<223> OTHER INFORMATION: Phosphorothioate linkage
<220> FEATURE:
<221> NAME/KEY: misc_feature
<222> LOCATION: (7)..(8), (8)..(9), (9)..(10), (10)..(11), (11)..(12),
        (12)..(13)
<223> OTHER INFORMATION: Phosphorothioate linkage
<220> FEATURE:
<221> NAME/KEY: misc_feature
<222> LOCATION: (1)..(1), (2)..(2), (11)..(11), (12)..(12), (13)..(13)
<223> OTHER INFORMATION: LNA

<400> SEQUENCE: 15
gcattggtat tca                                                        13

<210> SEQ ID NO 16
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6),
        (6)..(7), (7)..(8)
<223> OTHER INFORMATION: Phosphorothioate linkage
<220> FEATURE:
<221> NAME/KEY: misc_feature
<222> LOCATION: (8)..(9), (9)..(10), (10)..(11), (11)..(12), (12)..(13),
        (13)..(14)
<223> OTHER INFORMATION: Phosphorothioate linkage
<220> FEATURE:
<221> NAME/KEY: misc_feature
<222> LOCATION: (14)..(15), (15)..(16), (16)..(17), (17)..(18),
        (18)..(19)
<223> OTHER INFORMATION: Phosphorothioate linkage
<220> FEATURE:
<221> NAME/KEY: misc_feature
<222> LOCATION: (19)..(20)
<223> OTHER INFORMATION: Phosphorothioate linkage
<220> FEATURE:
<221> NAME/KEY: misc_feature
<222> LOCATION: (1)..(1), (2)..(2), (3)..(3), (4)..(4), (5)..(5),
        (16)..(16)
<223> OTHER INFORMATION: LNA
<220> FEATURE:
<221> NAME/KEY: misc_feature
<222> LOCATION: (17)..(17), (18)..(18), (19)..(19), (20)..(20)
<223> OTHER INFORMATION: LNA

<400> SEQUENCE: 16
tccagcattg gtattcagtg                                                 20

<210> SEQ ID NO 17
<211> LENGTH: 20
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6),
        (15)..(16)
<223> OTHER INFORMATION: Phosphorothioate linkage
<220> FEATURE:
<221> NAME/KEY: misc_feature
<222> LOCATION: (16)..(17), (17)..(18), (18)..(19), (19)..(20)
<223> OTHER INFORMATION: Phosphorothioate linkage
<220> FEATURE:
<221> NAME/KEY: misc_feature
<222> LOCATION: (1)..(1), (2)..(2), (3)..(3), (4)..(4), (5)..(5),
        (16)..(16)
<223> OTHER INFORMATION: 2-O-Me
<220> FEATURE:
<221> NAME/KEY: misc_feature
```

```
<222> LOCATION: (17)..(17), (18)..(18), (19)..(19), (20)..(20)
<223> OTHER INFORMATION: 2-O-Me

<400> SEQUENCE: 17
cacugaauac caaugcugga                                               20

<210> SEQ ID NO 18
<211> LENGTH: 13
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (11)..(12), (12)..(13)
<223> OTHER INFORMATION: Phosphorothioate linkage
<220> FEATURE:
<221> NAME/KEY: misc_feature
<222> LOCATION: (1)..(1), (2)..(2), (3)..(3), (12)..(12), (13)..(13)
<223> OTHER INFORMATION: 2-O-Me

<400> SEQUENCE: 18
ugaauaccaa ugc                                                      13

<210> SEQ ID NO 19
<211> LENGTH: 15
<212> TYPE: DNA
<213> ORGANISM: Artificial
<220> FEATURE:
<223> OTHER INFORMATION: Synthetic

<400> SEQUENCE: 19
tgaataccaa tgctg                                                    15
```

CHIMERIC SINGLE-STRANDED ANTISENSE POLYNUCLEOTIDES AND DOUBLE-STRANDED ANTISENSE AGENT

CROSS-REFERENCE TO RELATED APPLICATIONS

This application is a Divisional of U.S. application Ser. No. 14/771,252, which is the U.S. National Stage application of PCT/JP2014/001159, filed Mar. 3, 2014, which claims priority from U.S. Provisional Applications 61/771,115, filed Mar. 1, 2013; 61/806,887, filed Mar. 31, 2013; and 61/909,179, filed Nov. 26, 2013.

The instant application contains a Sequence Listing which has been submitted in ASCII format via EFS-WEB and is hereby incorporated by reference in its entirety. Said ASCII copy, created on Jun. 1, 2017, is named sequence.txt and is 14 KB.

TECHNICAL FIELD

The present application relates to a chimeric single-stranded polynucleotide and double-stranded antisense agent useful for modifying the expression of a target gene by means of an antisense effect. The chimeric single-stranded antisense polynucleotide comprises a central nucleotide region flanked by a first 5'-wing region and a first 3'-wing region of modified nucleotides, which are themselves flanked by a second 5'-wing region and/or a second 3'-wing region of nucleotides that have a low affinity for proteins and/or that have higher resistance to DNase or RNase than a natural DNA or RNA and are missing in a cell when the chimeric polynucleotide delivered. The double-stranded antisense agent comprises the chimeric single-stranded polynucleotide. The double-stranded antisense agent further comprises a complementary strand. The chimeric single-stranded polynucleotide and double-stranded antisense agent can be used to modify RNA transcription levels or protein levels in cells.

BACKGROUND

In recent years, oligonucleotides have been a subject of interest in the on-going development of pharmaceutical products called nucleic acid drugs, and particularly, from the viewpoints of high selectivity of target gene and low toxicity, the development of nucleic acid drugs utilizing an antisense method is actively underway. The antisense method includes methods of selectively modifying or inhibiting the expression of a protein that is encoded by a target gene, by introducing into a cell an oligonucleotide (antisense oligonucleotide (ASO) that is complementary to a partial sequence of the mRNA (sense strand) of a target gene. Similarly, antisense methods also target miRNA and operate to modify the activity of such miRNA.

As illustrated in FIG. 1 (upper portion), when an oligonucleotide comprising RNA is introduced into a cell as an ASO, the ASO binds to a transcription product (mRNA) of the target gene, and a partial double strand is formed. It is known that this double strand plays a role as a cover to prevent translation by a ribosome, and thus the expression of the protein encoded by the target gene is inhibited.

On the other hand, when an oligonucleotide comprising a DNA is introduced into a cell as an ASO, a partial DNA-RNA hetero-duplex is formed. Because this structure is recognized by RNase H, and the mRNA of the target gene is thereby decomposed, the expression of the protein encoded by the target gene is inhibited. (FIG. 1, lower portion). In many cases, the gene expression suppressing effect is higher when DNA is used as an ASO (RNase H-dependent route), as compared with the case of using an RNA ASO.

When utilizing an oligonucleotide as a nucleic acid drug, various nucleic acid analogs such as Locked Nucleic Acid (LNA) (registered trademark), other bridged nucleic acids (BNA), and the like have been developed to enhance binding affinity to target RNA and stability in vivo.

As illustrated in FIG. 2, since the sugar moiety of a natural nucleic acid (RNA or DNA) has a five-membered ring with four carbon atoms and one oxygen atom, the sugar moiety has two kinds of conformations, an N-form and an S-form. It is known that these conformations swing from one to the other, and thereby, the helical structure of the nucleic acid also adopts different forms, an A-form and a B-form. Since the mRNA that serves as the target of the aforementioned ASO adopts a helical structure in the A-form, with the sugar moiety being mainly in the N-form, it is important for the sugar moiety of the ASO to adopt the N-form from the viewpoint of increasing the affinity to RNA. A product that has been developed under this concept is a modified nucleic acid such as a LNA (2'-O,4'-C-methylene-bridged nucleic acid (2',4'-BNA)). For example, in the LNA, as the oxygen at the 2'-position and the carbon at the 4'-position are bridged by a methylene group, the conformation is fixed to the N-form, and there is no more fluctuation between the conformations. Therefore, an oligonucleotide synthesized by incorporating several units of LNA has very high affinity to RNA and very high sequence specificity, and also exhibits excellent heat resistance and nuclease resistance, as compared with oligonucleotides synthesized with conventional natural nucleic acids (see Patent Document 1). Since other artificial nucleic acids also have such characteristics, much attention has been paid to artificial nucleic acids in connection with the utilization of an antisense method and the like (see Patent Documents 1 to 9).

Nonetheless, the designs of antisense oligonucleotides using even these high-performance modified nucleic acids still lack suitable efficiency, potency, and/or safety for use as therapeutic agents.

It is known that the length of an ASO dramatically affects the performance of ASO's, but with two contrasting results. (Non-Patent Documents 5-7.) A longer probe length (e.g., 16-22 nucleotides) provides higher binding strength (higher Tm) and greater specificity for the targeted RNA sequence. The greater sequence specificity generally results in fewer side effects and little or no toxicity. However, the potency of longer probes is low. To compensate for such low activity, large doses are required.

In contrast, shorter probe lengths (e.g., 12-15 nucleotides) are the most potent—this length range generally provides the highest degree of suppression or inhibition of gene expression levels. The shorter probes, though, have lower sequence specificity and thus generally cause toxic side reactions.

Accordingly, there exists a need for polynucleotides that provide the efficiency and potency of a shorter ASO yet also have the safety of a longer ASO.

Furthermore, when an antisense oligonucleotide is used as a drug, it is important that the relevant oligonucleotide can be delivered to the target site with high specificity and high efficiency. Methods for delivering an oligonucleotide include using lipids such as cholesterol and vitamin E (Non-Patent Documents 1 and 2), using a receptor-specific peptide such as RVG-9R (Non-Patent Document 3), or using an antibody specific to the target site (Non-Patent Document 4).

CITATION LIST

Patent Document

Patent Document 1: JP 10-304889 A
Patent Document 2: WO 2005/021570
Patent Document 3: JP 10-195098 A
Patent Document 4: JP 2002-521310 W
Patent Document 5: WO 2007/143315
Patent Document 6: WO 2008/043753
Patent Document 7: WO 2008/029619
Patent Document 8: WO 2003/011887
Patent Document 9: WO 2007/131238

Non-Patent Document

Non-Patent Document 1: Kazutaka Nishina et al., Molecular Therapy, Vol. 16, 734-740 (2008)
Non-Patent Document 2: Jurgen Soutscheck et al., Nature, Vol. 432, 173-178 (2004)
Non-Patent Document 3: Kazutaka Nishina et al., Molecular Therapy, Vol. 16, 734-740 (2008)
Non-Patent Document 4: Dan Peer et al., Science, Vol. 319, 627-630 (2008)
Non-Patent Document 5: Ellen Marie Straarup et al., Nucleic Acids Research, Vol. 38(20), 7100-7111 (2010)
Non-Patent Document 6: Tsuyoshi Yamamoto et al., J. Nucleic Acids, Article ID 707323, 7 pages (2012)
Non-Patent Document 7: Jan Stenvang et al., Silence, Vol. 3:1, 17 pages (2012)

SUMMARY

A new chimeric antisense polynucleotide and the double-stranded antisense agent are provided which retains the efficacy and potency of shorter (~13 bases) polynucleotides despite having an increased length. The new chimeric antisense oligonucleotide comprises a short gapmer antisense oligonucleotide to which additional nucleotides are added at the 5' end, at the 3' end, or at both ends of the gapmer. The additional nucleotides display low affinity for protein binding. Otherwise, the additional nucleotides have higher DNase/RNase resistance than a natural DNA or RNA nucleotide and are missing in a cell when the chimeric antisense polynucleotide is delivered. The double-stranded antisense agent comprises the chimeric antisense polynucleotide. Thus, for example, a 13 base gapmer can be redesigned, according to the disclosure herein, as a 20 base gapmer that adds wing regions at one or both ends comprising nucleotides that display low binding affinity for proteins and protein-like cellular components, have higher DNase/RNase resistance than a natural DNA or RNA nucleotide and/or are missing in a cell when the chimeric antisense polynucleotide is delivered. The gapmer portion of the chimeric antisense strand, that is, the center region, the first 5'-wing region, and the first 3'-wing region may be any of the antisense strands described in PCT/JP2012/083180, entitled "Chimeric Double-Stranded Nucleic Acid," which is incorporated herein by reference in its entirety.

The inventors have determined that the new chimeric single-stranded polynucleotide and the double-stranded antisense agent, when introduced into a cell, can modify the activity or function of a transcription product. The transcription product may be a protein-encoding transcription product or a non-protein-encoding product such as miRNA. The application further contemplates methods for altering the expressed level of a protein in a cell, and for changing a protein structure by means of an antisense effect.

The chimeric antisense polynucleotide and the double-stranded antisense agent are also useful for treating patients having a condition characterized by an altered gene expression level, such that, for example, a protein is overexpressed. By treating the patient with a pharmaceutical composition comprising the chimeric antisense polynucleotide or the double-stranded antisense agent, the gene expression level can be specifically suppressed or inhibited to a degree that the protein levels decrease, thereby ameliorating the condition.

In certain embodiments, the following are provided.

(1) A chimeric antisense polynucleotide comprising:
a center nucleotide region comprising at least 5 nucleotides;
a first 5'-wing region joined to the 5' end of the center nucleotide region comprising 1-10 nucleotides wherein at least 1 is a nucleotide analog;
a first 3'-wing region joined to the 3' end of the center nucleotide region comprising 1-10 nucleotides wherein at least 1 is a nucleotide analog; and
a second 5'-wing region and/or a second 3'-wing region, wherein:
the second 5'-wing region is joined to the 5' end of the first 5'-wing region and comprises at least 1 low protein-affinity nucleotide; and
the second 3'-wing region is joined to the 3' end of the first 3'-wing region and comprises at least 1 low protein-affinity nucleotide;
wherein the total number of nucleotides, nucleotide analogs and low protein-affinity nucleotides is no more than 100 nucleotides.

(2) A chimeric antisense polynucleotide comprising:
a center nucleotide region comprising at least 5 nucleotides;
a first 5'-wing region joined to the 5' end of the center nucleotide region comprising 1-10 nucleotides wherein at least 1 is a nucleotide analog;
a first 3'-wing region joined to the 3' end of the center nucleotide region comprising 1-10 nucleotides wherein at least 1 is a nucleotide analog; and
a second 5'-wing region and/or a second 3'-wing region, wherein:
the second 5'-wing region is joined to the 5' end of the first 5'-wing region, has higher resistance to DNase or RNase than a natural DNA or RNA and is missing in a cell when the chimeric polynucleotide delivered; and
the second 3'-wing region is joined to the 3' end of the first 3'-wing region, has higher resistance to DNase or RNase than a natural DNA or RNA and is missing in a cell when the chimeric polynucleotide delivered,
wherein the total number of nucleotides and nucleotide analogs is no more than 100 nucleotides.

(3) The chimeric antisense polynucleotide of items (1 or 2), wherein the center nucleotide region comprises nucleotides that, when hybridized to an RNA polynucleotide, the center nucleotide region/RNA polynucleotide duplex is recognized by RNase H.

(4) The chimeric antisense polynucleotide of item (3), wherein the nucleotides of the center nucleotide region are independently selected from DNA and phosphorothioate DNA nucleotides.

(5) The chimeric antisense polynucleotide of item (4), wherein the center nucleotide region comprises 5-20 DNA nucleotides.

(6) The chimeric antisense polynucleotide of item (4), wherein the center nucleotide region comprises 5-12 DNA nucleotides.

(7) The chimeric antisense polynucleotide of items (1 or 2), wherein the center nucleotide region comprises nucleotides independently selected from RNA nucleotides and nucleotide analogs.

(8) The chimeric antisense polynucleotide of item (7), wherein the nucleotide analogs are independently selected from LNA nucleotides, BNA nucleotides, 2'-O-Me RNA nucleotides, 2'-O-methoxyethyl RNA nucleotides.

(9) The chimeric antisense polynucleotide of item (8), wherein the center nucleotide region comprises nucleotides independently selected from 2'-O-Me RNA nucleotides and 2'-O-methoxyethyl RNA nucleotides.

(10) The chimeric antisense polynucleotide of any one of items (1-9), wherein at least one of the nucleotides in the center nucleotide region is phosphorothioated.

(11) The chimeric antisense polynucleotide of item (10), wherein all nucleotides in the center nucleotide region are phosphorothioated.

(12) The chimeric antisense polynucleotide of any one of items (1-11), wherein the nucleotides in the first wing regions are bridged nucleotides.

(13) The chimeric antisense polynucleotide of any one of items (1-12), wherein the bridged nucleotides are independently selected from LNA, cEt BNA, amideBNA, and cMOE BNA.

(14) The chimeric antisense polynucleotides of any one of items (1-13), wherein at least one of the nucleotide analogs in the center nucleotide region and the first wing region(s) are phosphorothioated.

(15) The chimeric antisense polynucleotide of any one of items (1-14), wherein the low protein-affinity nucleotides are independently selected from 2'-O-methyl RNA nucleotides, 2'-O-methoxyethyl RNA nucleotides, LNA, cMOE BNA, 2-fluoro RNA nucleotides, boranophosphate nucleotides, methylphosphonate nucleotides, phosphoramidite nucleotides, 5-methylcytosine, UNA and 5-propynyluridine.

(16) The chimeric antisense polynucleotide of any one of items (1-15), wherein the chimeric antisense polynucleotide includes the second 5'-wing region.

(17) The chimeric antisense polynucleotide of any one of items (1-15), wherein the chimeric polynucleotide includes the second 3'-wing region.

(18) The chimeric antisense polynucleotide of any one of items (1-15), wherein the chimeric antisense polynucleotide includes the second 5'-wing region and the second 3'-wing region.

(19) The chimeric antisense polynucleotide of any one of items (1-18), wherein the chimeric antisense polynucleotide further comprises a functional moiety joined to the 3'-end and/or the 5'-end of the chimeric antisense polynucleotide.

(20) The chimeric antisense polynucleotide of item (19), wherein the functional moiety has a function selected from a labeling function, a purification function, and a targeted delivery function.

(21) The chimeric antisense polynucleotide of item (19), wherein the functional moiety is joined to the chimeric antisense polynucleotide via a cleavable linker moiety.

(22) The chimeric antisense polynucleotide of item (19), wherein the functional moiety is a molecule selected from a lipid, a peptide, and a protein.

(23) The chimeric antisense polynucleotides of item (22), wherein the lipid is selected from cholesterol, a fatty acid, a lipid-soluble vitamin, a glycolipid, and a glyceride.

(24) The chimeric antisense polynucleotides of item (22), wherein the lipid is selected from cholesterol, a tocopherol, and a tocotrienol.

(25) The chimeric antisense polynucleotides of item (22), wherein the peptide is selected from a receptor ligand fragment and an antibody fragment.

(26) The chimeric antisense polynucleotide of item (22), wherein the protein is selected from a receptor ligand and an antibody.

(27) The chimeric antisense polynucleotide of item (1 or 2), wherein the chimeric antisense polynucleotide can hybridize to a cellular transcription product in a 100 mM sodium chloride, 10 mM sodium phosphate buffer, pH 7.2, at 25° C.

(28) The chimeric antisense polynucleotide of item (27), wherein the center region is fully complementary to the cellular transcription product to which the chimeric antisense polynucleotide can hybridize.

(29) The chimeric antisense polynucleotide of item (27), wherein the second 5'-wing region and/or the second 3'-wing region comprise at least one mismatched base when the chimeric antisense polynucleotide hybridizes to the cellular transcription product to which the chimeric antisense polynucleotide can hybridize.

(30) The chimeric antisense polynucleotide of item (29), wherein all bases of the second 5'-wing region and/or the second 3'-wing region are mismatched.

(31) A double-stranded antisense agent comprising the chimeric antisense polynucleotide of any one of items (1-18) and (27-30) and a complementary strand annealed to the chimeric antisense polynucleotide.

(32) The double-stranded antisense agent comprising the chimeric antisense polynucleotide of item (31), wherein the complementary strand further comprises a functional moiety joined to the 3'-end and/or the 5'-end.

(33) The double-stranded antisense agent of item (32), wherein the functional moiety has a function independently selected from a labeling function, a purification function, and a targeted delivery function.

(34) The double-stranded antisense agent of item (32), wherein the functional moiety is independently joined to the chimeric antisense polynucleotide and/or the complementary strand via a cleavable linker moiety.

(35) The double-stranded antisense agent of item (32), wherein the functional moiety is a molecule independently selected from a lipid, a peptide, and a protein.

(36) The double-stranded antisense agent of item (35), wherein the lipid is independently selected from cholesterol, a fatty acid, a lipid-soluble vitamin, a glycolipid, and a glyceride.

(37) The double-stranded antisense agent of item (35), wherein the lipid is independently selected from cholesterol, a tocopherol, and a tocotrienol.

(38) The double-stranded antisense agent of item (35), wherein the peptide is independently selected from a receptor ligand fragment and an antibody fragment.

(39) The double-stranded antisense agent of item (35), wherein the protein is independently selected from a receptor ligand and an antibody.

(40) The double-stranded antisense agent comprising the chimeric antisense polynucleotide of item (31), wherein the chimeric antisense polynucleotide can hybridize to a cellular transcription product in a 100 mM sodium chloride, 10 mM sodium phosphate buffer, pH 7.2, at 25° C.

(41) A pharmaceutical composition comprising the chimeric antisense polynucleotide of any one of items (1-30) or the double-stranded antisense agent of any one of items (31-40), and a pharmaceutically acceptable carrier.

(42) A method of modifying the function of a transcription product in a cell comprising the step of administering to the cell a composition comprising the chimeric antisense polynucleotide of any one of items (1-30) or the double-stranded antisense agent of any one of items (31-40).

(43) A method of changing the expressed level of a protein in a cell comprising the step of administering to the cell a composition comprising the chimeric antisense polynucleotide of any one of items (1-30) or the double-stranded antisense agent of any one of items (31-40).

(44) A method of changing a protein structure in a cell comprising the step of administering to the cell a composition comprising the chimeric antisense polynucleotide of any one of items (1-30) or the double-stranded antisense agent of any one of items (31-40).

(45) A method for treating a patient having a condition characterized by changing expression level, function or editing of a target gene, comprising:
  administering to said patient a therapeutically effective amount of a pharmaceutical composition comprising
  (a) at least one chimeric antisense polynucleotide of any one of items (1-30) or the double-stranded antisense agent of any one of items (31-40); and
  (b) a pharmaceutically acceptable carrier.

According to certain embodiments, a chimeric antisense polynucleotide can be delivered to a target site with high specificity and high efficiency by associating a delivery moiety with the complex. According to certain embodiments, a double-stranded antisense agent can be delivered to a target site with high specificity and high efficiency by associating a functional moiety, e.g., a delivery moiety, with the double-stranded complex.

BRIEF DESCRIPTION OF DRAWINGS

FIGS. 4A-4D are schematic diagrams illustrating examples of suitable embodiments of chimeric polynucleotides. The chimeric polynucleotide 5'-($2^{nd}$ 5' wing) ($1^{st}$ 5' wing) (center region) ($1^{st}$ 3' wing) ($2^{nd}$ 3' wing)-3' strands are antisense nucleic acids that can hybridize to targeted RNA strands, such as a transcription product. In the illustrations, "X" represents a functional moiety, and may independently represent a lipid (for example, cholesterol or tocopherol), a sugar or the like, or a protein, a peptide (for example, an antibody) or the like.

FIGS. 6A-6D are schematic diagrams illustrating designs for chimeric winged antisense oligonucleotides that incorporate sequence mismatches into the 5' and 3' second wing regions as a means for tuning the potency of the antisense effect.

FIG. 8A shows the sequence of two gapmer antisense polynucleotides and three chimeric winged antisense polynucleotides, and a schematic illustration comparing the design of each polynucleotide.

FIG. 9 is a graph illustrating the results obtained by administering the chimeric polynucleotides and control polynucleotides, shown in the upper portion of the figure, to mice, and analyzing the amounts of expression of ApoB1 gene, whose transcription product is targeted by the antisense strand, in the mice.

FIG. 16A shows the sequence of gapmer antisense polynucleotides and a chimeric antisense polynucleotide targeting ApoB1, and complementary nucleotides used to form double-stranded antisense agents with the antisense polynucleotides.

Figure 1:
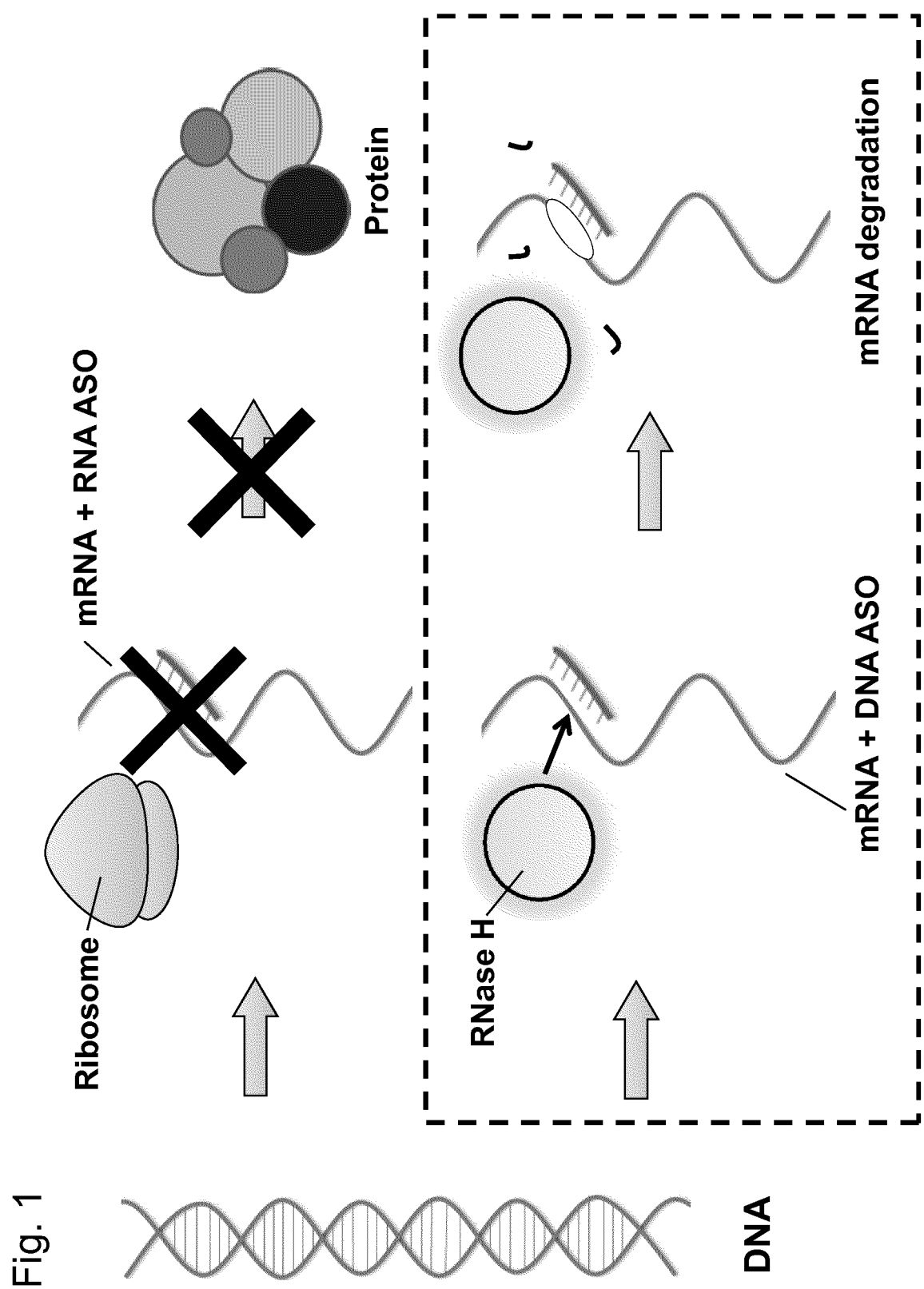
FIG. 1 is a diagram illustrating the general mechanisms of certain antisense methods. As illustrated in the diagram, when an oligonucleotide (antisense oligonucleotide (ASO)) ("DNA" in the diagram) that is complementary to a partial sequence of the mRNA of a target gene is introduced into a cell, the expression of a protein that is encoded by the target gene is selectively inhibited. In the dashed box, a degradation mechanism is shown in which RNase H cleaves mRNA at a location at which it is hybridized to an ASO. As a result of RNase H cleavage, the mRNA generally will not be translated to produce a functional gene expression product.
Figure 2:
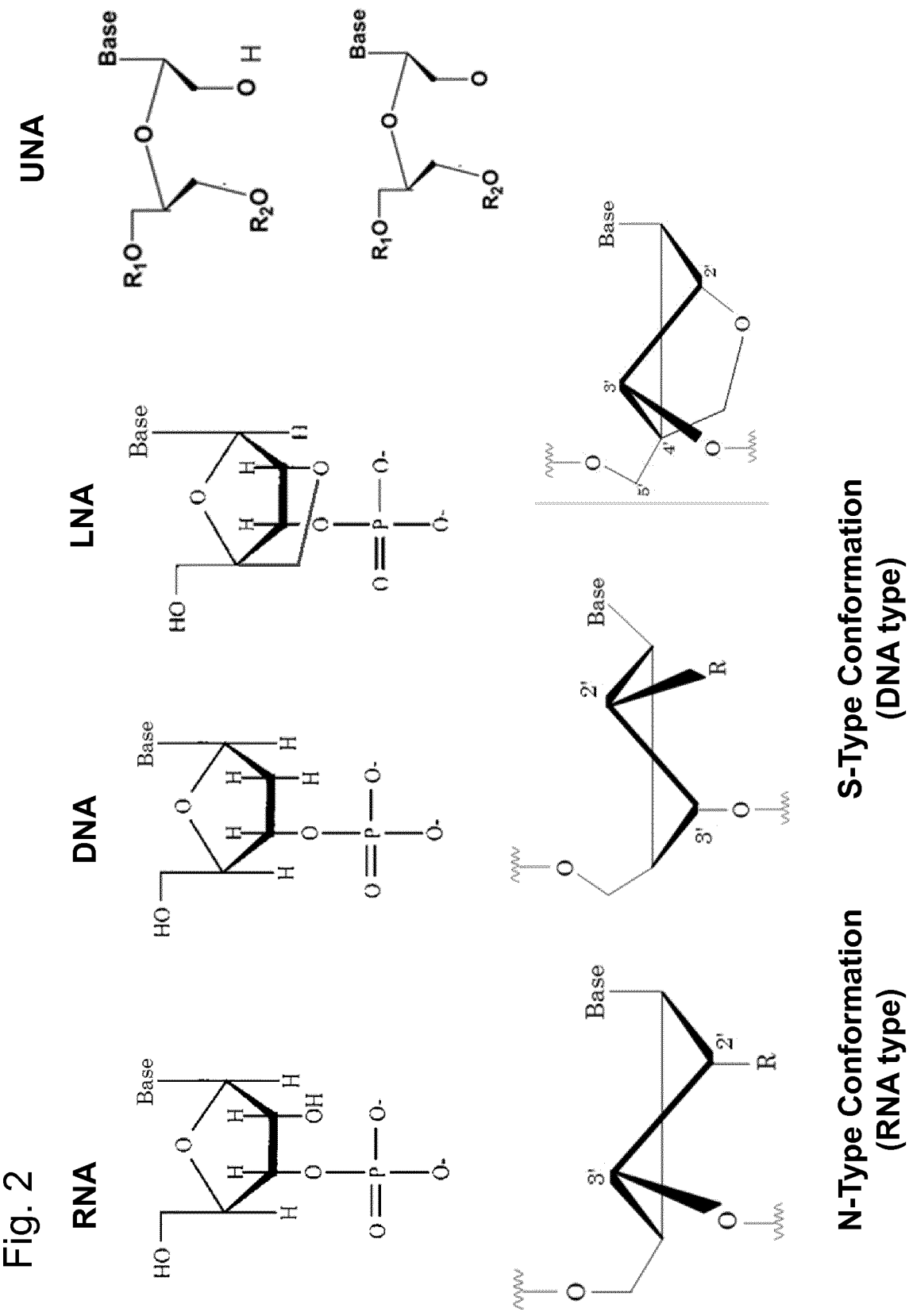
FIG. 2 is a schematic diagram illustrating the structures of RNA, DNA, and an LNA nucleotide.

Chimeric single-stranded polynucleotides comprising the following structure are active in modifying or suppressing the expression of a target gene or more generally the level of a transcription product, by means of an antisense effect:

a center nucleotide region comprising at least 5 nucleotides;

a first 5'-wing region joined to the 5' end of the center nucleotide region comprising 1-10 nucleotide analogs;

a first 3'-wing region joined to the 3' end of the center nucleotide region comprising 1-10 nucleotide analogs; and a second 5'-wing region and/or a second 3'-wing region, wherein:

the second 5'-wing region is joined to the 5' end of the first 5'-wing region and comprises at least 1 low protein-affinity nucleotide; and the second 3'-wing region is joined to the 3' end of the first 3'-wing region and comprises at least 1 low protein-affinity nucleotide;

wherein the total number of nucleotides, nucleotide analogs, and low protein-affinity nucleotides is no more than 100 nucleotides.

Otherwise, chimeric single-stranded polynucleotides comprising the following structure are active in modifying or suppressing the expression of a target gene or more generally the level of a transcription product, by means of an antisense effect:

a center nucleotide region comprising at least 5 nucleotides;

a first 5'-wing region joined to the 5' end of the center nucleotide region comprising 1-10 nucleotides wherein at least 1 is a nucleotide analog;

a first 3'-wing region joined to the 3' end of the center nucleotide region comprising 1-10 nucleotides wherein at least 1 is a nucleotide analog; and a second 5'-wing region and/or a second 3'-wing region, wherein:

the second 5'-wing region is joined to the 5' end of the first 5'-wing region, has higher resistance to DNase or RNase than a natural DNA or RNA and is missing in a cell when the chimeric polynucleotide delivered; and the second 3'-wing region is joined to the 3' end of the first 3'-wing region, has higher resistance to DNase or RNase than a natural DNA or RNA and is missing in a cell when the chimeric polynucleotide delivered, wherein the total number of nucleotides and nucleotide analogs is no more than 100 nucleotides.

Certain embodiments include a purified or isolated double-stranded antisense agent comprising the chimeric single stranded antisense polynucleotide above.

In some embodiments, the center nucleotide region of the antisense strand comprises at least 4 consecutive nucleotides, or in some embodiments at 5 least consecutive nucleotides, that are recognized by RNase H when the antisense strand is hybridized to a transcription product.

The complementary strand comprises nucleotides and optionally nucleotide analogs, and optionally a low protein-affinity nucleotide, and the complementary strand can anneal to the antisense strand.

In some embodiments the complementary strand comprises:

(i) an RNA nucleotide and optionally a nucleotide analog, and optionally a low protein-affinity nucleotide, and optionally a DNA nucleotide; or (ii) a DNA nucleotide and/or a nucleotide analog and/or a low protein-affinity nucleotide; or (iii) PNA nucleotides.

The "antisense effect" means suppressing the expression of a target gene or the level of a targeted transcription product, which occurs as a result of hybridization of the targeted transcription product (RNA sense strand) with, for example, a DNA strand, or more generally, a strand designed to cause the antisense effect, complementary to a partial sequence of the transcription product or the like. In certain instances, inhibition of translation or a splicing function modifying effect such as exon skipping (see the description in the upper part outside the area surrounded by dotted lines in FIG. 1) may be caused by covering of the transcription product by the hybridization product, and/or decomposition of the transcription product may occur as a result of recognition of the hybridized portion (see the description within the area surrounded by dotted lines in FIG. 1).

The "target gene" or "targeted transcription product" whose expression is suppressed by the antisense effect is not particularly limited, and examples thereof include genes whose expression is increased in various diseases. Also, the "transcription product of the target gene" is an mRNA transcribed from the genomic DNA that encodes the target gene, and also includes an mRNA that has not been subjected to base modification, a mRNA precursor that has not been spliced, and the like. More generally, the "transcription product" may be any RNA synthesized by a DNA-dependent RNA polymerase.

As used herein, the term "nucleic acid" may refer to a monomeric nucleotide or nucleoside, or may mean an oligonucleotide consisting of plural monomers. The term "polynucleotide" and "nucleic acid strand" is also used herein to refer to an oligonucleotide. Nucleic acid strands may be prepared in whole or in part by chemical synthesis methods, including using a automated synthesizer or by enzymatic processes, including but not limited to polymerase, ligase, or restriction reactions.

The term "chimeric polynucleotide" as used herein means a polynucleotide that comprises at least one natural nucleotide (e.g., DNA or RNA nucleotide) and at least one non-natural nucleotide (e.g., LNA, 2'-O-methyl RNA), or is comprised entirely of non-natural nucleotides, and as a result is a polynucleotide that does not occur in nature. The chimeric polynucleotide according to certain embodiments is an antisense oligonucleotide complementary to a transcription product, such as that of a target gene.

The term "chimeric antisense polynucleotide" or "chimeric ASO" means a chimeric polynucleotide that comprises a sequence complementary to the targeted transcription product.

The term "double-stranded antisense agent" means a double-stranded polynucleotide complex that can cause an antisense effect. A double-stranded antisense agent can comprise two or more polynucleotide strands. In some embodiments the strands are annealed. In some embodiments, the agent comprises two strands, an antisense strand and a complementary strand, the two of which can anneal to form a double-stranded complex. The antisense strand is a chimeric polynucleotide (described below). The complementary strand is, in some embodiments, a chimeric polynucleotide, and in other embodiments consists of natural nucleotides, and in other embodiments comprises peptide nucleic acid units.

The term "complementary" as used herein means a relationship in which so-called Watson-Crick base pairs (natural type base pair) or non-Watson-Crick base pairs (Hoogsteen base pairs and the like) can be formed via hydrogen bonding. It is not necessary that the base sequence of the targeted transcription product, e.g., the transcription product of a target gene, and the base sequence of the chimeric antisense polynucleotide be perfectly complementary, and it is acceptable if the base sequences have a complementarity of at least 70% or higher, preferably 80% or higher, and more preferably 90% or higher (for example, 95%, 96%, 97%, 98%, or 99% or higher). The complementarity of sequences can be determined by using a BLAST program or the like. A first strand can be "annealed" or "hybridized" to a second strand when the sequences are complementary. A person of ordinary skill in the art can readily determine the conditions (temperature, salt concentration, etc.) under which two strands can be annealed, taking into account the degree of complementarity between the strands. Also, a person having ordinary skill in the art can readily design an antisense nucleic acid complementary to the targeted transcription product based on the information of the base sequence of, e.g., the target gene.

The strand length of the chimeric antisense polynucleotide is not particularly limited, but the strand length is usually at least 8 bases, at least 10 bases, at least 12 bases, or at least 13 bases. The strand length may be up to 20 bases, 25 bases, or 35 bases. The strand length may even be as long as about 100 bases. Ranges of the length may be 10 to 35 bases, 12 to 25 bases, or 13 to 20 bases. In certain instances, the choice of length generally depends on a balance of the strength of the antisense effect with the specificity of the nucleic acid strand for the target, among other factors such as cost, synthetic yield, and the like.

In some embodiments, the choice of the length of the chimeric ASO and the degree of complementarity between it and the target strand may also depend on the binding affinity between the chimeric ASO and the target strand after it has been cleaved by RNase H. The potency of an ASO depends both on the binding affinity of the ASO with the target prior to cleavage as well as the off-rate for the cleaved material to dissociate from the ASO so it is freed to bind to another target strand.

The chimeric antisense polynucleotide comprises a "center region," a "first 5'-wing region," and a "first 3'-wing region." The chimeric polynucleotide further comprises a "second 5'-wing region" or a "second 3'-wing region," or both. These regions are further explained below. The assignment of a particular nucleotide to one such region or another is not exclusive. There may be several ways to assign the nucleotides of a given polynucleotide to the different regions. These region names are for convenience, although it should be apparent that by preparing a sequence wherein the nucleotides provide such regions the polynucleotide will achieve the functional performance described herein.

The "center region" comprises both natural and non-natural nucleotides. The type of nucleotides selected for the center region largely determines the type of antisense mechanism(s) of action that are possible. For example, including DNA and/or DNA-like nucleotides in the center region may lead to the formation of DNA/RNA heteroduplex structures that can be recognized by RNase H. Thus, RNase H-dependent mechanism of action is possible in this case. On the other hand, if DNA and/or DNA-like nucleotides are excluded from the center region, then RNase H-independent mechanisms of action are expected to occur. Of course, even if DNA/RNA heteroduplex structures are formed, RNase H-independent mechanisms may occur.

In some embodiments, the center region comprises at least 5 nucleotides that "when hybridized to an RNA polynucleotide, the center nucleotide region/RNA polynucleotide duplex is recognized by Rnase H."

The "at least 5 nucleotides" that when hybridized to RNA are "recognized by RNase H" is usually a region comprising 5 to 20 consecutive bases, a region comprising 5 to 16 consecutive bases, a region comprising 5 to 12 consecutive bases, or a region comprising 5 to 8 consecutive bases. Furthermore, nucleotides that may be used in this region are those that, like natural DNA, are recognized by RNase H when hybridized to RNA nucleotides, wherein the RNase H cleaves the RNA strand. Suitable nucleotides, such as modified DNA nucleotides and other bases are known in the art. Nucleotides that contain a 2'-hydroxy group, like an RNA nucleotide are known to not be suitable. One of skill in the art can readily determine the suitability of a nucleotide for use in this region of "at least 5 nucleotides" when an RNase H-dependent effect is desired. In one embodiment, the nucleotides of the center nucleotide region are independently selected from DNA and phosphorothioate DNA nucleotides.

In some embodiments, the center region may comprises as few as 4 nucleotides that when hybridized to an RNA polynucleotide, the center nucleotide region/RNA polynucleotide duplex is recognized by RNase H.

In other embodiments, the center region does not comprise DNA. That is, in certain embodiments, an antisense nucleic acid has an RNase H-independent effect, or, alternatively, a non-RNase H-dependent antisense effect. The "non-RNase H-dependent antisense effect" means an activity of suppressing the expression of a target gene that occurs as a result of inhibition of translation or a splicing function modifying effect such as exon skipping when a transcription product of the target gene (RNA sense strand) and a nucleic acid strand that is complementary to a partial sequence of the transcription product are hybridized (see the description of the upper part outside the area surrounded by dotted lines in FIG. 1).

The "nucleic acid that does not comprise DNA" means an antisense nucleic acid that does not comprise natural DNA and modified DNA, and an example thereof may be RNA, modified RNA, nucleotide analogs, a PNA, or a nucleic acid comprising morpholino nucleic acid. Furthermore, in regard to the "nucleic acid that does not comprise DNA," a portion or the entirety of the nucleic acid may be composed of modified nucleotides and/or nucleotide analogs, from the viewpoint that the resistance to nucleases is high. Examples of such modification include those described below, and the same nucleotide may be subjected to plural kinds of modifications in combination. Furthermore, preferred embodiments related to the number of modified nucleic acids and the position of modification can be characterized by measuring the antisense effect possessed by the chimeric polynucleotide after modification, as described below.

It is not necessary that the base sequence of the nucleotides in the center region and the base sequence of the transcription product of a target gene be perfectly complementary to each other, and the base sequences may have a complementarity of at least 70% or higher, preferably 80% or higher, and more preferably 90% or higher (for example, 95%, 96%, 97%, 98%, 99% or higher).

There are no particular limitations on the length of the "nucleic acid that does not comprise DNA," but the length is as described above, and is usually 5 to 35 bases, 5 to 25 bases, 12 to 25 bases, or 13 to 20 bases.

There are no particular limitations on the length of the "nucleic acid that does not comprise DNA," but the length is as described above, and is usually 5 to 35 bases, 5 to 25 bases, 12 to 25 bases, or 13 to 20 bases.

As used herein, "DNA nucleotide" means a natural DNA nucleotide, or a DNA nucleotide with a modified base, sugar, or phosphate linkage subunit. Similarly, "RNA nucleotide" means a natural RNA nucleotide, or an RNA nucleotide with a modified base, sugar, or phosphate linkage subunit. A modified base, sugar, or phosphate linkage subunit is one in which a single substituent has been added or substituted in a subunit, and the subunit as a whole has not been replaced with a different chemical group. From the viewpoint that a portion or the entirety of the region comprising the nucleotide has high resistance to deoxyribonuclease and the like, the DNA may be a modified nucleotide. Examples of such modification include 5-methylation, 5-fluorination, 5-bromination, 5-iodination, and N4-methylation of cytosine; 5-demethylation, 5-fluorination, 5-bromination, and 5-iodination of thymidine; N6-methylation and 8-bromination of adenine; N2-methylation and 8-bromination of guanine; phosphorothioation, methylphosphonation, methylthiophosphonation, chiral methylphosphonation, phosphorodithioation, phosphoroamidation, 2'-O-methylation, 2'-methoxyethyl(MOE)ation, 2'-aminopropyl(AP)ation, and 2'-fluorination. However, from the viewpoint of having excellent pharmacokinetics, phosphorothioation is preferred. Such modification may be carried out such that the same DNA may be subjected to plural kinds of modifications in combination. And, as discussed below, RNA nucleotides may be modified to achieve a similar effect.

In certain instances, the number of modified DNA's and the position of modification may affect the antisense effect and the like provided by the chimeric antisense polynucleotide as disclosed herein. Since these embodiments may vary with the sequence of the target gene and the like, it may depend on cases, but a person having ordinary skill in the art can determine suitable embodiments by referring to the descriptions of documents related to antisense methods. Furthermore, when the antisense effect possessed by a chimeric antisense polynucleotide after modification is measured, if the measured value thus obtained is not significantly lower than the measured value of the chimeric antisense polynucleotide before modification (for example, if the measured value obtained after modification is lower by 30% or more than the measured value of the chimeric antisense polynucleotide before modification), the relevant modification can be evaluated. The measurement of the antisense effect can be carried out, as indicated in the Examples below, by introducing a nucleic acid compound under test into a cell or the like, and measuring the amount of expression (amount of mRNA, amount of cDNA, amount of a protein, or the like) of the target gene in the cell in which the expression is suppressed by the antisense effect provided by the nucleic acid compound under test, by appropriately using known techniques such as Northern Blotting, quantitative PCR, and Western Blotting. The candidate agent may be the chimeric antisense polynucleotide itself, or as part of a double-stranded antisense agent.

As used herein, "RNA nucleotide" means a naturally occurring RNA nucleotide, or an RNA nucleotide with a modified base, sugar, or phosphate linkage subunit. A modified base, sugar, or phosphate linkage subunit is one in which a single substituent has been added or substituted in a subunit, and the subunit as a whole has not been replaced with a different chemical group.

A portion or the entirety of the nucleic acid may be a modified nucleotide, from the viewpoint of having high resistance to a nuclease such as a ribonuclease (RNase). Examples of such modification include 5-methylation, 5-fluorination, 5-bromination, 5-iodination and N4-methylation of cytosine; 5-demethylation, 5-fluorination, 5-bromination, and 5-iodination of thymidine; N6-methylation and 8-bromination of adenine; N2-methylation and 8-bromination of guanine; phosphorothioation, methylphosphonation, methylthiophosphonation, chiral methylphosphonation, phosphorodithioation, phosphoroamidation, 2'-O-methylation, 2'-methoxyethyl(MOE)ation, 2'-aminopropyl(AP) lation, cleavage between 2'-carbon and 3'-carbon of deoxyribose (resulting in 'UNA') and 2'-fluorination. Also, an RNA nucleotide with a thymidine base substituted for a uracil base is also contemplated. However, from the viewpoint of having excellent pharmacokinetics, phosphorothioation is used. Furthermore, such modification may be carried out such that the same nucleic acid may be subjected to plural kinds of modifications in combination. For example, as used in the Examples described below, the same RNA may be subjected to phosphorothioation and 2'-O-methylation in order to provide resistance to enzymatic cleavage.

As used herein, "nucleotide analog" means a non-naturally occurring nucleotide, wherein the base, sugar, or phosphate linkage subunit has more than one substituent added or substituted in a subunit, or that the subunit as a whole has been replaced with a different chemical group. An example of an analog with more than one substitution is a bridged nucleic acid, wherein a bridging unit has been added by virtue of two substitutions on the sugar ring, typically linked to the 2' and 4' carbon atoms. In regard to the first wing according to certain embodiments, from the viewpoint of increasing the affinity to a partial sequence of the transcription product of the target gene and/or the resistance of the target gene to a nuclease, the first wing further comprises a nucleotide analog. The "nucleotide analog" may be any nucleic acid in which, owing to the modifications (bridging groups, substituents, etc.), the affinity to a partial sequence of the transcription product of the target gene and/or the resistance of the nucleic acid to a nuclease is enhanced, and examples thereof include nucleic acids that are disclosed to be suitable for use in antisense methods, in JP 10-304889 A, WO 2005/021570, JP 10-195098 A, JP 2002-521310 W, WO 2007/143315, WO 2008/043753, WO 2008/029619, and WO 2008/049085 (hereinafter, these documents will be referred to as "documents related to antisense methods"). That is, examples thereof include the nucleic acids disclosed in the documents described above: a hexitol nucleic acid (HNA), a cyclohexane nucleic acid (CeNA), a peptide nucleic acid (PNA), a glycol nucleic acid (GNA), a threose nucleic acid (TNA), a morpholino nucleic acid, a tricyclo-DNA (tcDNA), a 2'-O-methylated nucleic acid, a 2'-MOE (2'-O-methoxyethyl)lated nucleic acid, a 2'-AP (2'-O-aminopropyl)lated nucleic acid, a 2'-fluorinated nucleic acid, a 2'-F-arabinonucleic acid (2'-F-ANA), and a BNA (bridged nucleic acid).

The BNA according to certain embodiments may be any ribonucleotide or deoxyribonucleotide in which the 2' carbon atom and 4' carbon atom are bridged by two or more atoms. Examples of bridged nucleic acids are known to those of skill in the art. One subgroup of such BNA's can be described as having the carbon atom at the 2'-position and the carbon atom at the 4'-position bridged by 4'-$(CH_2)_p$—O-2',4'-$(CH_2)_p$—S-2',4'-$(CH_2)_p$—OCO-2',4'-$(CH_2)_n$—N($R_3$)—O—$(CH_2)_m$-2' (here, p, m and n represent an integer from 1 to 4, an integer from 0 to 2, and an integer from 1 to 3, respectively; and $R_3$ represents a hydrogen atom, an alkyl group, an alkenyl group, a cycloalkyl group, an aryl group, an aralkyl group, an acyl group, a sulfonyl group, and a unit substituent (a fluorescent or chemiluminescent labeling molecule, a functional group having nucleic acid cleavage activity, an intracellular or intranuclear localization signal peptide, or the like)). Furthermore, in regard to the BNA according to certain embodiments, in the $OR_2$ substituent on the carbon atom at the 3'-position and the $OR_1$ substituent on the carbon atom at the 5'-position, $R_1$ and $R_2$ are typically hydrogen atoms, but may be identical with or different from each other, and may also be a protective group of a hydroxyl group for nucleic acid synthesis, an alkyl group, an alkenyl group, a cycloalkyl group, an aryl group, an aralkyl group, an acyl group, a sulfonyl group, a silyl group, a phosphoric acid group, a phosphoric acid group protected by a protective group for nucleic acid synthesis, or —P($R_4$)$R_5$ (here, $R_4$ and $R_5$, which may be identical with or different from each other, each represent a hydroxyl group, a hydroxyl group protected by a protective group for nucleic acid synthesis, a mercapto group, a mercapto group protected by a protective group for nucleic acid synthesis, an amino group, an alkoxy group having 1 to 5 carbon atoms, an alkylthio group having 1 to 5 carbon atoms, a cyanoalkoxy group having 1 to 6 carbon atoms, or an amino group substituted with an alkyl group having 1 to 5 carbon atoms). Non-limiting examples of such a BNA include α-L-methyleneoxy(4'-$CH_2$—O-2') BNA or β-D-methyleneoxy(4'-$CH_2$—O-2')BNA, which are also known as LNA (Locked Nucleic Acid (registered trademark), 2',4'-BNA), ethyleneoxy(4'-$CH_2$)$_2$—O-2')BNA which is also known as ENA, β-D-thio(4'-$CH_2$—S-2')BNA, aminooxy(4'-$CH_2$—O—N($R_3$)-2')BNA, oxyamino(4'-$CH_2$—N($R_3$)—O-2')BNA which is also known as 2',4'-BNA$^{NC}$, 2',4'-BNA$^{COC}$, 3'-amino-2',4'-BNA, 5'-methyl BNA, (4'-CH($CH_3$)—O-2')BNA, which is also known as cEt BNA, (4'-CH($CH_2OCH_3$)—O-2')BNA, which is also known as cMOE BNA, amideBNA (4'-C(O)—N(R)-2')BNA (R=H, Me), which is also known as AmNA, and other BNA's known to those of skill in the art.

The unlocked nucleic acids (UNA) according to certain embodiments may be any ribonucleotide or deoxyribonucleotide in which the covalent bond between 2' carbon atom and 3' carbon atom are cleaved to give rise to increase flexibility. Examples of unlocked nucleic acids are known to those of skill in the art.

Furthermore, in the nucleotide analog, according to certain embodiments, a base moiety may be modified. Examples of the modification at a base moiety include 5-methylation, 5-fluorination, 5-bromination, 5-iodination, and N4-methylation of cytosine; 5-demethylation, 5-fluorination, 5-bromination, and 5-iodination of thymidine; N6-methylation and 8-bromination of adenine; and N2-methylation and 8-bromination of guanine. Furthermore, in the modified nucleic acid according to certain embodiments, a phosphoric acid diester binding site may be modified. Examples of the modification of the phosphoric acid diester binding site include phosphorothioation, methylphosphonation, methylthiophosphonation, chiral methylphosphonation, phosphorodithioation, and phosphoroamidation. However, from the viewpoint of having excellent pharmacokinetics, phosphorothioation may be used, for example, in the central region and the first wing region. Also, such modification of a base moiety or modification of a phosphoric acid diester binding site may be carried out such that the same nucleic acid may be subjected to plural kinds of modifications in combination.

Figure 5:
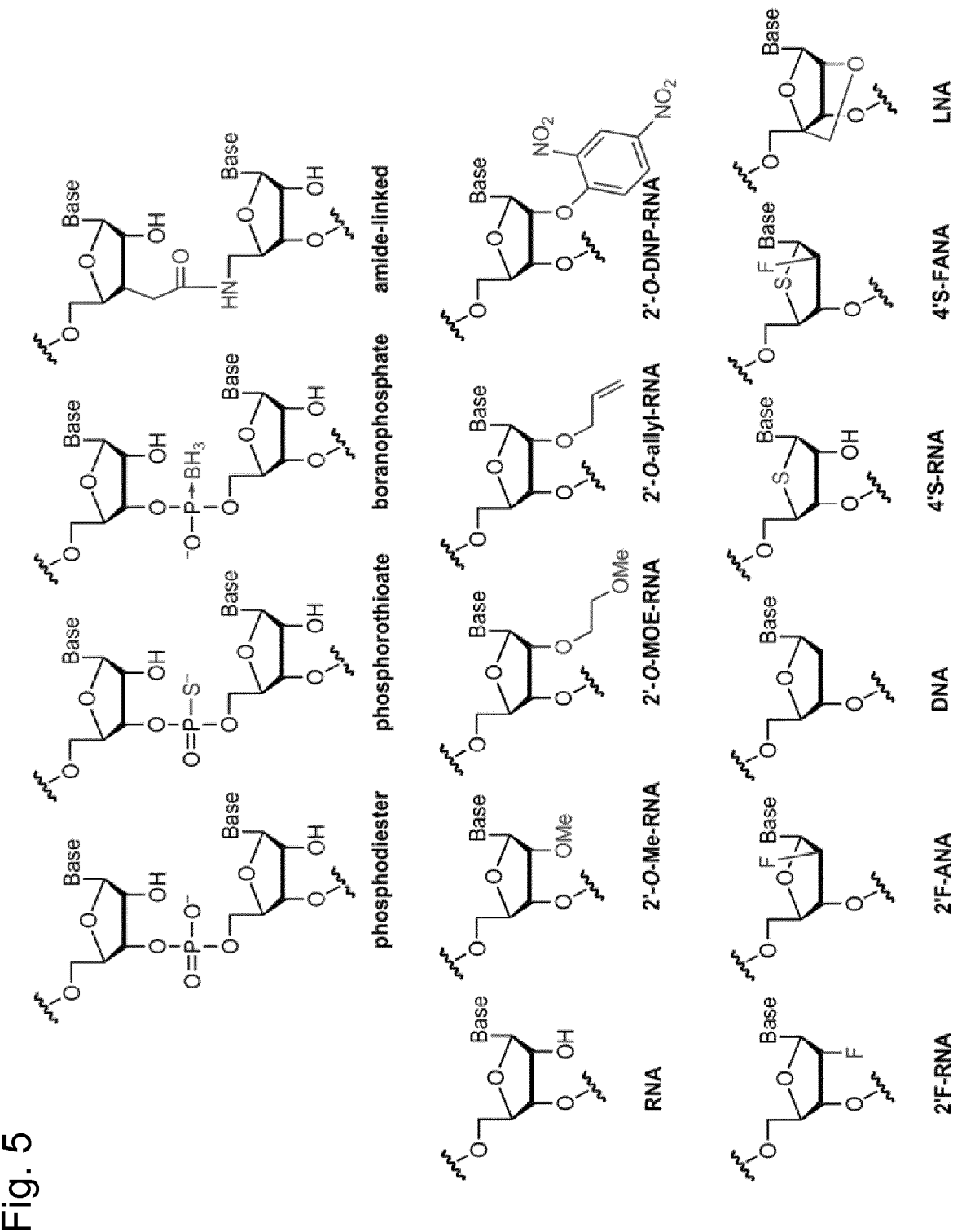
FIG. 5 shows the structural formula of various natural and non-natural nucleic acid moieties.

Generally, modified nucleotides and modified nucleotide analogs are not limited to those exemplified herein. Numerous modified nucleotides and modified nucleotide analogs are known in art, such as, for example those disclosed in U.S. Pat. No. 8,299,039 to Tachas et al., particularly at col. 17-22, and may be used in the embodiments of this application. Examples of a natural nucleotides, modified nucleotides, and nucleotide analogs are shown in FIG. 5.

A person having ordinary skill in the art can appropriately select and use a nucleotide analog among such modified nucleic acids while taking consideration of the antisense effect, affinity to a partial sequence of the transcription product of the target gene, resistance to a nuclease, and the like. However, the nucleotide analog in some embodiments is a LNA represented by the following formula (1):

[Chemical Formula 1]

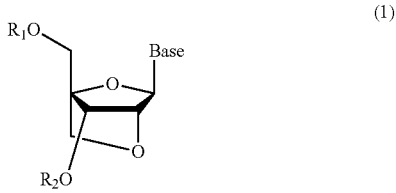

(1)

In formula (1), "Base" represents an aromatic heterocyclic group or aromatic hydrocarbon ring group which may be substituted, for example, a base moiety (purine base or pyrimidine base) of a natural nucleoside, or a base moiety of a non-natural (modified) nucleoside, while examples of modification of the base moiety include those described above; and $R_1$ and $R_2$, which may be identical with or different from each other, each represent a hydrogen atom, a protective group of a hydroxyl group for nucleic acid synthesis, an alkyl group, an alkenyl group, a cycloalkyl group, an aryl group, an aralkyl group, an acyl group, a sulfonyl group, a silyl group, a phosphoric acid group, a phosphoric acid group protected by a protective group for nucleic acid synthesis, or —P($R_4$)$R_5$ [here, $R_4$ and $R_5$, which may be identical or different from each other, each represent a hydroxyl group, a hydroxyl group protected by a protective group for nucleic acid synthesis, a mercapto group, a mercapto group protected by a protective group for nucleic acid synthesis, an amino group, an alkoxy group having 1 to 5 carbon atoms, an alkylthio group having 1 to 5 carbon atoms, a cyanoalkoxy group having 1 to 6 carbon atoms, or an amino group substituted with an alkyl group having 1 to 5 carbon atoms.

The compounds shown by the above chemical formulas are represented as nucleosides, but the "LNA" and more generally, the BNA according to certain embodiments include nucleotide forms in which a phosphoric acid derived group is bound to the relevant nucleoside (nucleotide). In other words, BNA's, such as LNA, are incorporated as nucleotides in the nucleic strands that comprise the double stranded nucleic acid complex.

Furthermore, the nucleotide analog in some embodiments is a unlocked nucleic acid (UNA) represented by the following formula (2) and (3):

[Chemical Formula 2]

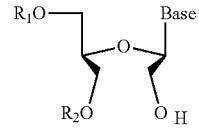

[Chemical Formula 3]

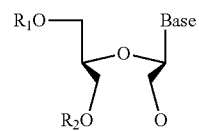

The unlocked nucleic acid (UNA) oligonucleotides are flexible RNA mimics that enable them to modulate their affinity to other nucleotides and specificity. The unlocked nucleic acid UNA are an acyclic-RNA analogues and are also known as 2',3'-seco-RNA of which the C2'-C3' bond are cleaved. The bound cleavage make them flexible and give rise to them modulation of the thermodynamic stability of various nucleic acid.

The "first 5'-wing region" and the "first 3'-wing region" are, according to certain embodiments, located on the 5' side and the 3' side, respectively, and continuously linked to the terminal nucleotide on the respective ends of the center region.

The region comprising a nucleotide analog that is disposed immediately to the 5'-side of the center region (hereinafter, also called "first 5' wing region") and the region comprising a nucleotide analog that is disposed immediately to the 3'-side of the center region (hereinafter, also called "first 3' wing region") may each independently comprise at least one kind of a nucleotide analog that is discussed in the documents related to antisense methods, and may further comprise a natural nucleic acid (DNA or RNA) in addition to such a nucleotide analog. Furthermore, the strand lengths of the first 5' wing region and the first 3' wing region are independently usually 1 to 10 bases, 1 to 7 bases, or 2 to 5 bases.

Furthermore, there are suitable embodiments of the number of kinds and position of the nucleotide analog and the natural nucleotide in the first 5' wing region and the first 3' wing region, since the number and the position of those nucleic acids may affect the antisense effect and the like provided by the double-stranded nucleic acid complex in certain embodiments. Since these suitable embodiments may vary with the sequence and the like, it may depend on cases, but a person having ordinary skill in the art can determine the suitable embodiments by referring to the descriptions of documents related to antisense methods. Furthermore, when the antisense effect possessed by the antisense strand alone or by the double-stranded antisense agent after modification is measured in the same manner as in the case of the region comprising "at least 5 nucleotides," if the measured value thus obtained is not significantly lower than that of the strand or the agent before modification, the relevant modification can be evaluated as a preferred embodiment.

Figure 3A:
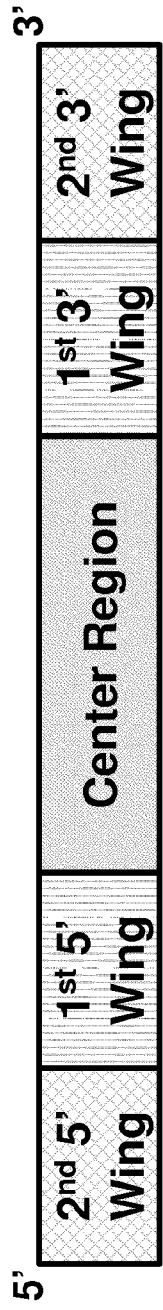
FIGS. 3A-3C are schematic diagrams illustrating examples of suitable embodiments of chimeric polynucleotides. The core 5'-($1^{st}$ 5' wing) (center region) ($1^{st}$ 3' wing)-3' may be joined with both a ($2^{nd}$ 5' wing) and a ($2^{nd}$ 3' wing) (FIG. 3A), only a ($2^{nd}$ 5' wing) (FIG. 3B), or only a ($2^{nd}$ 3' wing) (FIG. 3C).
Figure 3B:
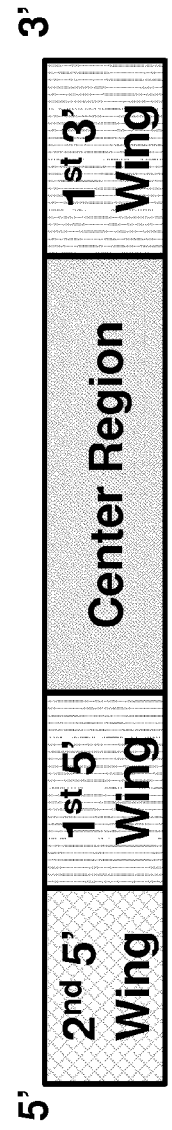
Figure 3C:

As noted above, the chimeric antisense polynucleotide comprises at least one "second wing" region. Some embodiments may comprise just one second wing region, at either the 5' end or the 3' end of the polynucleotide, or the chimeric antisense polynucleotide may comprise both a second 5'-wing region and a second 3'-wing region. These structural designs are illustrated in FIGS. 3A-3C.

The "second 5'-wing region" and "second 3'-wing region," if present, comprise at least 1 low protein-affinity nucleotide.

A "low protein-affinity nucleotide" is a nucleotide that is (i) more resistant to DNase or RNase than a natural DNA or RNA nucleotide and (ii) possesses low affinity for binding to protein or protein-like cellular components. In particular, the nucleotide has a lower binding affinity towards proteins than a phosphorothioated nucleotide. Accordingly, a low protein-affinity nucleotide is a modified nucleotide or a nucleotide analog as described above, but the nucleotide is not phosphorothioated.

Examples of low protein-affinity nucleotides include 2'-O-methyl RNA nucleotides, 2'-O-methoxyethyl RNA nucleotides, LNA, cMOE BNA, 2-fluoro RNA nucleotides, boranophosphate nucleotides, methylphosphonate nucleotides, phosphoramidite nucleotides, 5-methylcytosine, unlocked nucleic acids(UNA) and 5-propynyluridine.

The second wings as disclosed herein extend the length of the subject chimeric polynucleotides beyond the length that is usually desired for ASO's. However, described here and in the examples below, by including low protein-affinity nucleotides in the second wing region(s), the performance decrease usually observed in longer length ASO's is reduced or even eliminated. In other words, the degree of gene expression inhibition that can be achieved with the chimeric antisense polynucleotides described herein approaches the performance of conventional gapmer ASO's that do not have a second wing region(s) are thus necessarily shorter in length. And, the degree of gene expression inhibition that can be achieved with the double-stranded antisense agents described herein approaches, equals, and in some embodiments exceeds the performance of conventional single-stranded gapmer ASO's that do not have a second wing region(s) are thus necessarily shorter in length.

The length of each second wing region is independent. There is no particular limitation on the length of each second wing, other than the overall limitation on the entire length of the chimeric antisense polynucleotide being no more than 100 nucleotides.

It may be desirable to adjust the binding affinity of the bases in the second wing region(s). At one extreme, the nucleotides in the second wing region(s) can be selected to be fully complementary to the targeted sequence in the transcription product. Or, the second wing region(s) sequence can be completely mismatched with respect to the corresponding target. And, any combination of matched and mismatched base pairs in the second wing region(s) is also contemplated. These options are schematically illustrated in FIGS. 6A-6D. It is known in the art that the binding affinity is an important consideration in the performance of antisense inhibition. As discussed in Non-Patent Document 6, there is an optimum range of binding affinity between an ASO and a target for achieving maximum potency of the ASO. Accordingly, the length, base content, and pattern of matched and mismatched base incorporated into the second 5'-wing region and the second 3'-wing region can be optimized for use according to the embodiments disclosed herein.

The complementary strand according to some embodiments is a polynucleotide complementary to the chimeric antisense polynucleotide described above. It is not necessary that the base sequence of the complementary strand and the base sequence of the chimeric antisense strand be perfectly complementary to each other, and the base sequences may have a complementarity of at least 70% or higher, preferably 80% or higher, and more preferably 90% or higher (for example, 95%, 96%, 97%, 98%, 99% or higher).

The complementary strand is a polynucleotide comprising at least one kind of nucleic acid selected from RNA, DNA, PNA (peptide nucleic acid) and BNA (e.g., LNA). More specifically, the complementary strand comprises (i) an RNA nucleotide and optionally a nucleotide analog, and optionally a low protein-affinity nucleotide, and optionally a DNA nucleotide; or (ii) a DNA nucleotide and/or a nucleotide analog and/or a low protein-affinity nucleotide; or (iii) PNA nucleotides.

The term "RNA nucleotides and optionally nucleotide analogs, and optionally a low protein-affinity nucleotide, and optionally a DNA nucleotide" means that the complementary strand includes RNA nucleotides, and optionally may further include nucleotide analogs in the strand, and optionally may further include low protein-affinity nucleotides in the strand, and optionally may further include DNA nucleotides in the strand. The term "DNA nucleotides and/or nucleotide analogs and/or a low protein-affinity nucleotide" means that the second strand may include either DNA nucleotides or nucleotide analogs, or low protein-affinity nucleotides, or may include some combination of DNA nucleotides, nucleotide analogs, or low protein-affinity nucleotides. The term "PNA nucleotides" means that the second strand may substantially comprise PNA nucleotides, although other nucleotides may be included.

When the double-stranded antisense agent of certain embodiments is recognized by RNase H in the cell and the complementary nucleic acid strand is thus decomposed, releasing the chimeric antisense strand, the second nucleic acid strand generally comprises RNA nucleotides. In some embodiments, from the viewpoint that a functional molecule such as a peptide can be easily bound to the double-stranded complex, the second nucleic acid strand comprises PNA.

The length of the complementary strand is not particularly limited. The complementary strand may be shorter than, the same size as, or longer than the chimeric antisense polynucleotide. In some embodiments, a complementary strand that can anneal to two or more chimeric antisense polynucleotides is used. The two or more chimeric antisense strands may target the same sequence or different sequences.

In some embodiments, the double-stranded antisense agent comprises more than two polynucleotides. For example, two antisense strands may form a double-stranded complex with one complementary strand. Various multicomponent double-stranded complexes are disclosed in PCT/JP2012/083180, and those may also be applied to the double-stranded antisense agents disclosed in this application.

In some embodiments, the complementary polynucleotide comprises in whole or in part modified nucleotides or nucleotide analogs that are, compared to natural nucleotides, resistant to a nuclease such as a ribonuclease (RNase). Examples of such modification include 5-methylation, 5-fluorination, 5-bromination, 5-iodination and N4-methylation of cytosine; 5-demethylation, 5-fluorination, 5-bromination, and 5-iodination of thymidine; N6-methylation and 8-bromination of adenine; N2-methylation and 8-bromination of guanine; phosphorothioation, methylphosphonation, methylthiophosphonation, chiral methylphosphonation, phosphorodithioation, phosphoroamidation, 2'-O-methylation, 2'-methoxyethyl(MOE)ation, 2'-aminopropyl(AP) lation, and 2'-fluorination. Also, an RNA nucleotide with a thymidine base substituted for a uracil base is also contemplated. The low protein-affinity nucleotides may also be incorporated in the complementary strand. However, in some embodiments, phosphorothioation is used. Furthermore, such modification may be carried out such that the same nucleic acid may be subjected to plural kinds of modifications in combination. For example, as used in the Examples described below, the same RNA may be subjected to phosphorothioation and 2'-O-methylation in order to provide resistance to enzymatic cleavage. However, where it is expected or desired for an RNA nucleotide to be cleaved by RNase H, then only either phosphorothioation or 2'-O-methylation is generally applied.

There are suitable embodiments of the number of nucleotide analogs and the position of modification within the complementary strand, since the number and the position of modification may affect the antisense effect and the like provided by the double-stranded antisense agent in certain embodiments. Since these suitable embodiments may vary with the type, sequence and the like of the nucleic acid to be modified, it may depend on the circumstances, but the type, sequence and the like can be characterized by measuring the antisense effect possessed by the double-stranded antisense agent after modification in the same manner as described above.

In some embodiments, from the viewpoint that while the decomposition by a ribonuclease such as RNase A is suppressed until the complementary strand is delivered into the nucleus of a particular cell, the complementary strand can easily exhibit the antisense effect by being decomposed by RNase H in the particular cell, the complementary strand generally comprises RNA, and nucleotides that increase the nuclease stability and/or the $T_m$ may be incorporated. For example, in the region of the complementary strand that is complementary to one of the wing regions of the chimeric antisense strand (i.e., a first or second 5' wing region and/or a first or second 3' wing region), one may optionally incorporate one or more modified nucleic acids, one or more nucleotide analogs, and/or one or more low protein-affinity nucleotides, which serves to suppress decomposition of the complex by enzymes, such as a ribonuclease.

Figure 15:
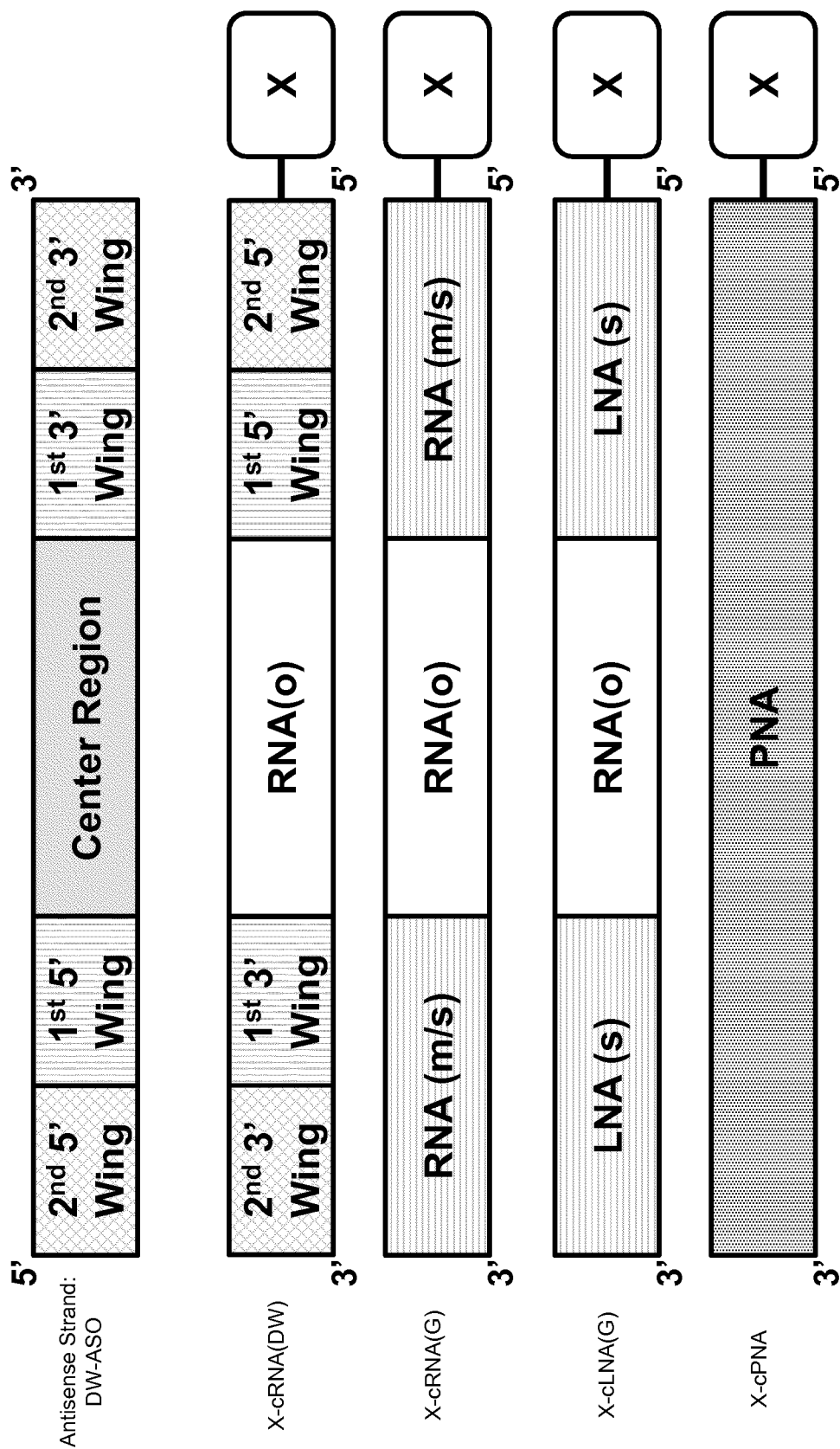
FIG. 15 presents schematic diagrams of an embodiment of a chimeric antisense oligonucleotide and example embodiments of suitable complementary strands.

According to certain embodiments, the modification is 2'-O-methylation and/or phosphorothioation of RNA. Furthermore, in some embodiments, the entire region of the complementary strand that is complementary to one of the wing regions of the antisense strand may be modified, or a portion of the region that is complementary to the wing regions of the antisense strand may be modified. In addition, the region that is modified may be longer than the region comprising a modified nucleic acid of the first nucleic acid strand, or may be shorter, as long as the region that is modified comprises that portion. Examples of some embodiments of the structure of the complementary strand in relation to the structure of the antisense strand are shown in FIG. 15. First, the upper structure is a double wing antisense polynucleotide (DW-ASO). Below that are four examples of complementary strands. For example, where it is desired that the double-stranded agent be susceptible to cleavage by RNase H, then the portion of the complementary strand that is complementary to the center region preferably comprises RNA. (RNA(o)=RNA with diphosphate linkage). The portions of the complementary strand that are complementary to the various wing regions of the DW-ASO may also comprise modified nucleotides and/or nucleotide analogues. For example, the double wing structure may also be included in the complementary strand (cRNA(DW)). Or, the portions of the complementary strand that are complementary to the first and second wing regions at each end may comprise modified nucleotides and/or nucleotide analogues, though not necessarily low protein-affinity nucleotides (cRNA(G) or cLNA (G); G referring to a "gapmer" structure). Or, the complementary strand may comprise peptide nucleic acids. FIG. 6 presents a simplified view of the structure, and the various complementary regions do not necessarily have to be in registration. One of skill in art can readily understand that the structure can be modified without departing from the desired functionality of the double-stranded antisense agent, including the functionality of the constituent polynucleotides. Finally, the complementary strands shown in FIG. 15 include a functional group "X" at the 5' terminus. Such a group is optionally included, and is described below.

In the double-stranded antisense agent, one or more of the constituent polynucleotides may further comprise a functional moiety.

In some embodiments, the strand complementary to the antisense polynucleotide may comprise a functional moiety bonded to the polynucleotide. Referring back to FIG. 15, a functional moiety "X" is illustrated joined to the 5'-end of the various examples of complementary strands. The functional moiety, further described below, could alternatively be joined at the 3'-end, or at a position internal to the polynucleotide. In other embodiments, the complementary strand comprises more than one functional moiety, which may be joined at a plurality of positions, and/or joined as a group to one position of the polynucleotide.

Figure 4A:
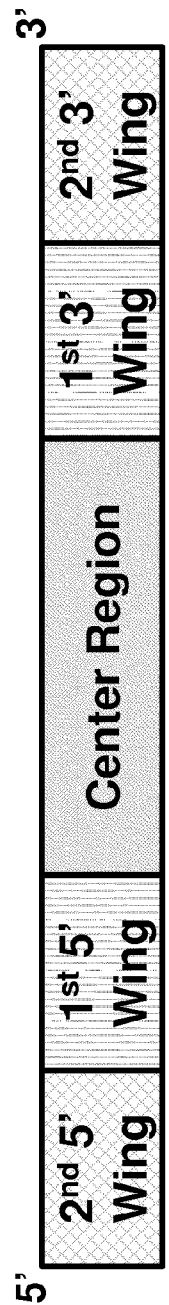
Figure 4B:
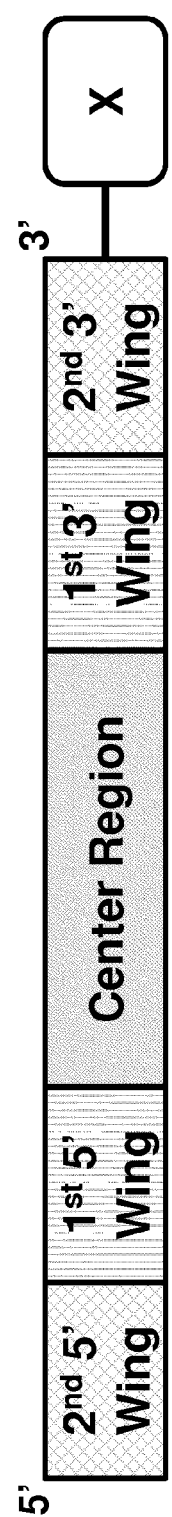
Figure 4C:
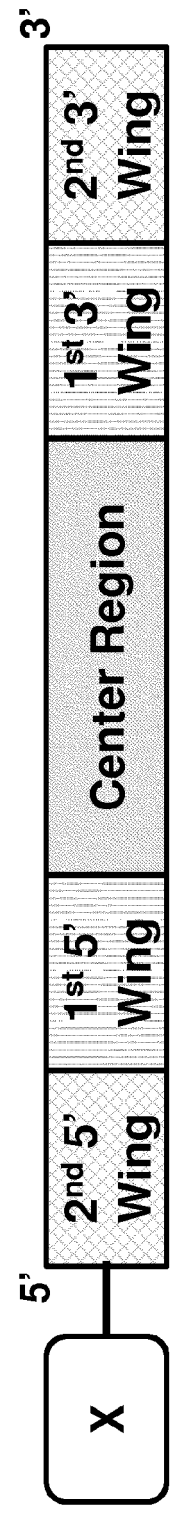
Figure 4D:
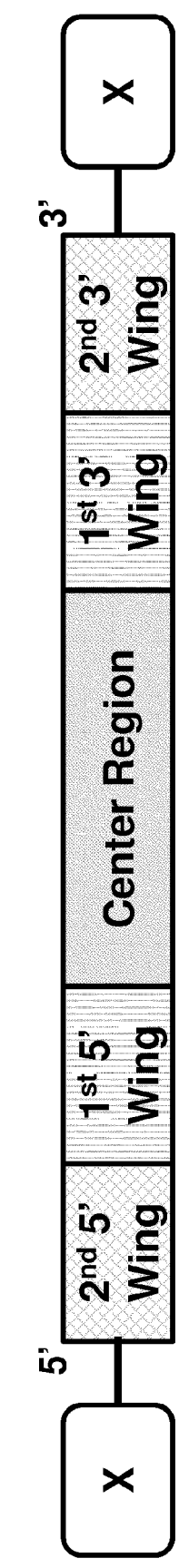

In some embodiments, the chimeric antisense polynucleotide may comprise a functional moiety bonded to the polynucleotide. For example, the functional moiety may be joined to the 5'-terminal nucleotide, or the 3'-terminal nucleotide, or to both the 5' and 3' terminal nucleotides of the chimeric antisense polynucleotide, as illustrated in FIGS. 4B, 4C, and 4D. Of course, the functional moiety could also be joined to an internal position, and more than one moiety could be joined, as described above.

In the chimeric antisense polynucleotide of certain embodiments, a functional moiety may be bonded to the polynucleotide. The bonding between the polynucleotide (e.g., antisense polynucleotide or complementary polynucleotide) and the functional moiety may be direct bonding, or may be indirect bonding mediated by another material. However, in certain embodiments, it is preferable that a functional moiety be directly bonded to the polynucleotide such as the second wing via covalent bonding, ionic bonding, hydrogen bonding or the like, and from the viewpoint that more stable bonding may be obtained, covalent bonding is more preferred. The functional moiety may also be bonded to the polynucleotide via a cleavable linking group. For example, the functional moiety may be linked via a disulfide bond.

There are no particular limitations on the structure of the "functional moiety" according to certain embodiments, provided it imparts the desired function to the chimeric polynucleotide. The desired functions include a labeling function, a purification function, and a delivery function. Examples of moieties that provide a labeling function include compounds such as fluorescent proteins, luciferase, and the like. Examples of moieties that provide a purification function include compounds such as biotin, avidin, a His tag peptide, a GST tag peptide, a FLAG tag peptide, and the like.

Furthermore, from the viewpoint of delivering the chimeric polynucleotide to a target site with high specificity and high efficiency, and thereby suppressing very effectively the expression of a target gene by the relevant nucleic acid, it is preferable that a molecule having an activity of delivering the chimeric antisense polynucleotide of some embodiments to a "target site" within the body, be bonded as a functional moiety to the chimeric antisense polynucleotide and/or another polynucleotide constituent of the double-stranded antisense agent. In some embodiments, it is preferred that the functional moiety is joined to the complementary strand, that is, the polynucleotide complementary to and annealed to the antisense polynucleotide.

The moiety having a "targeted delivery function" may be, for example, a lipid, from the viewpoint of being capable of delivering the chimeric polynucleotide of certain embodiments to the liver or the like with high specificity and high efficiency. Examples of such a lipid include lipids such as cholesterol and fatty acids (for example, vitamin E (tocopherols, tocotrienols), vitamin A, and vitamin D); lipid-soluble vitamins such as vitamin K (for example, acylcarnitine); intermediate metabolites such as acyl-CoA; glycolipids, glycerides, and derivatives thereof. However, among these, from the viewpoint of having higher safety, in certain embodiments, cholesterol and vitamin E (tocopherols and tocotrienols) are used. Furthermore, from the viewpoint of being capable of delivering the chimeric antisense polynucleotide of certain embodiments to the brain with high specificity and high efficiency, examples of the "functional moiety" according to the certain embodiments include sugars (for example, glucose and sucrose). Also, from the viewpoint of being capable of delivering the chimeric antisense polynucleotide of certain embodiments to various organs with high specificity and high efficiency by binding to the various proteins present on the cell surface of the various organs, examples of the "functional moiety" according to certain embodiments include peptides or proteins such as receptor ligands and antibodies and/or fragments thereof.

In regard to the chimeric antisense polynucleotide of certain embodiments, the functional moiety may be joined to the 5'-terminal nucleotide, or the 3'-terminal nucleotide, or to both the 5' and 3' terminal nucleotides, as illustrated in FIGS. 4B, 4C, and 4D. Techniques for coupling labels to a nucleic acid strand vary with the nature of the labeling moiety and the point of attachment in the nucleic acid, and these are well-known in the art. Although not illustrated, functional moieties may be joined to the polynucleotide at internal sites and not at the strand terminal sites. Again, such techniques are well-known in the art.

Thus, some suitable exemplary embodiments of the chimeric polynucleotide of some embodiments have been described, but the chimeric polynucleotide is not intended to be limited to the exemplary embodiments described above. Furthermore, any person having ordinary skill in the art can produce the chimeric polynucleotide according to the various embodiments by appropriately selecting a known method. For example, the nucleic acids according to some embodiments can be produced by designing the respective base sequences of the nucleic acids on the basis of the information of the base sequence of the targeted transcription product (or, in some cases, the base sequence of a targeted gene), synthesizing the nucleic acids by using a commercially available automated nucleic acid synthesizer (products of Applied Biosystems, Inc.; products of Beckman Coulter, Inc.; and the like), and subsequently purifying the resulting oligonucleotides by using a reverse phase column or the like. Nucleic acids produced in this manner are mixed in an appropriate buffer solution and denatured at about 90° C. to 98° C. for several minutes (for example, for 5 minutes), subsequently the nucleic acids are annealed at about 30° C. to 70° C. for about 1 to 8 hours, and thus the double-stranded nucleic acid complex of some embodiments can be produced. Furthermore, a polynucleotide bearing a functional moiety can be produced by joining a functional moiety to the oligonucleotide strand during or after the oligonucleotide synthesis. Numerous methods for joining functional moieties to nucleic acids are well-known in the art.

Thus, suitable exemplary embodiments of the chimeric single-stranded antisense polynucleotide the complementary polynucleotide have been described. Additional embodiments are also disclosed in the following Examples. However, the chimeric polynucleotide and the double-stranded antisense agent as contemplated by the inventors is not limited to the exemplary embodiments described above, or in the Examples below.

Compositions for modifying the expression of target gene or level of targeted transcription product by means of antisense effect are also contemplated.

The chimeric single-stranded polynucleotide and the double stranded antisense agent of some embodiments can be delivered to a target site with high specificity and high efficiency and can very effectively suppress the expression of a target gene or the level of a transcription product, as will be disclosed in the Examples described below. Therefore, some embodiments provide a composition that contains the chimeric antisense polynucleotide or the double stranded antisense agent of some embodiments as an active ingredient and is intended to modify or suppress, e.g., the expression of a target gene by means of an antisense effect. Particularly, the chimeric antisense polynucleotides or the double stranded antisense agent of some embodiments can give high efficacy even when administered at a low concentration, and the chimeric design also displays reduced toxicity. Further, by directing the antisense polynucleotide or the double stranded antisense agent to particular organs, adverse side effects can be reduced. Therefore, some embodiments can also provide a pharmaceutical composition intended to treat and prevent diseases that are associated with, e.g., increased expression of a target gene, such as metabolic diseases, tumors, and infections.

The composition containing the chimeric antisense polynucleotides or the double stranded antisense agent of some embodiments can be formulated by known pharmaceutical methods. For example, the composition can be used enterally (perorally or the like) in the form of capsules, tablets, pills, liquids, powders, granules, fine granules, film-coating agents, pellets, troches, sublingual agents, peptizers, buccal preparations, pastes, syrups, suspensions, elixirs, emulsions, coating agents, ointments, plasters, cataplasms, transdermal preparations, lotions, inhalers, aerosols, injections and suppositories, or non-enterally.

In regard to the formulation of these preparations, pharmacologically acceptable carriers or carriers acceptable as food and drink, specifically sterilized water, physiological saline, vegetable oils, solvents, bases, emulsifiers, suspending agents, surfactants, pH adjusting agents, stabilizers, flavors, fragrances, excipients, vehicles, antiseptics, binders, diluents, isotonizing agents, soothing agents, extending agents, disintegrants, buffering agents, coating agents, lubricating agents, colorants, sweetening agents, thickening agents, corrigents, dissolution aids, and other additives can be appropriately incorporated.

On the occasion of formulation, as disclosed in Non-Patent Document 1, the chimeric antisense polynucleotides or the double-stranded antisense agent of some embodiments to which a lipid is bound as a functional moiety may be caused to form a complex with a lipoprotein, such as chylomicron or chylomicron remnant. Furthermore, from the viewpoint of increasing the efficiency of enteral administration, complexes (mixed micelles and emulsions) with substances having a colonic mucosal epithelial permeability enhancing action (for example, medium-chain fatty acids, long-chain unsaturated fatty acids, or derivatives thereof (salts, ester forms or ether forms)) and surfactants (nonionic surfactants and anionic surfactants) may also be used, in addition to the lipoproteins.

There are no particular limitations on the preferred form of administration of the composition of some embodiments, and examples thereof include enteral (peroral or the like) or non-enteral administration, more specifically, intravenous administration, intraarterial administration, intraperitoneal administration, subcutaneous administration, intracutaneous administration, tracheobronchial administration, rectal administration, and intramuscular administration, and administration by transfusion.

The composition of some embodiments can be used for animals including human beings as subjects. However, there are no particular limitations on the animals excluding human beings, and various domestic animals, domestic fowls, pets, experimental animals and the like can be the subjects of some embodiments.

When the composition of some embodiments is administered or ingested, the amount of administration or the amount of ingestion may be appropriately selected in accordance with the age, body weight, symptoms and health condition of the subject, type of the composition (pharmaceutical product, food and drink, or the like), and the like. However, the effective amount of ingestion of the composition according to the certain embodiments is 0.001 mg/kg/day to 50 mg/kg/day of the chimeric polynucleotide.

The chimeric polynucleotides or the double stranded antisense agent of some embodiments can be delivered to a target site with high specificity and high efficiency, and can modify or suppress the expression of a target gene or the level of a transcription product very effectively, as will be disclosed in the Examples that follow. Therefore, some embodiments can provide a method of administering the chimeric polynucleotides or the double stranded antisense agent of some embodiments to a subject, and suppressing the expression of a target gene or transcription product level by means of an antisense effect. Furthermore, a method of treating or preventing various diseases that are associated with, e.g., increased expression of target genes, by administering the composition of some embodiments to a subject can also be provided.

EXAMPLES

Hereinafter, some embodiments will be described more specifically by way of Examples, but the embodiments not intended to be limited to the following Examples.

Example 1

Figure 7:
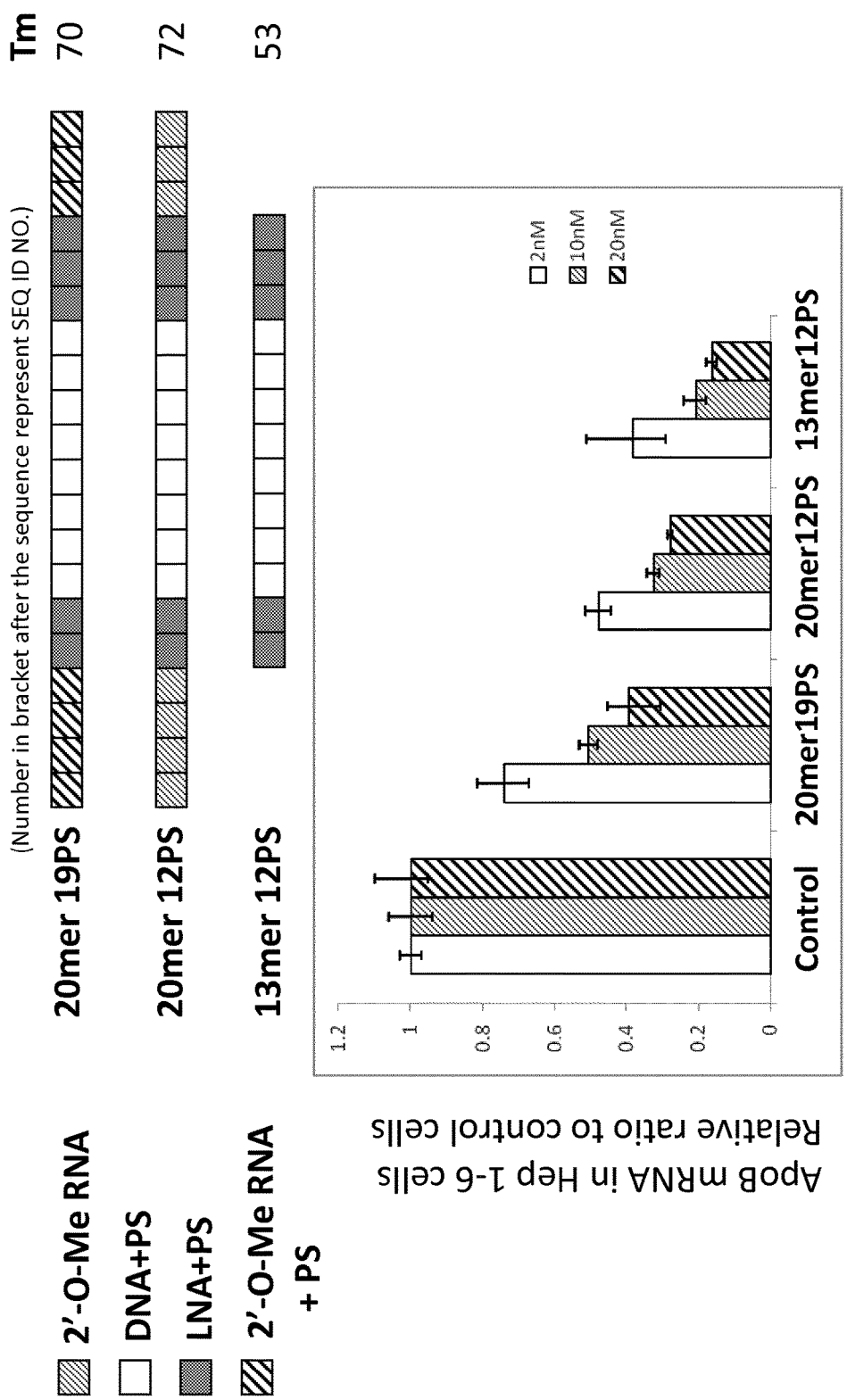
FIG. 7 shows a graph illustrating the results obtained upon administering to Hep 1-6 cells "20mer19PS," "20mer12PS," and "13mer12PS," all of which have a sequence complementary to the base sequence of ApoB1 gene, and analyzing the amount of expression of ApoB1 gene in the cells by quantitative PCR, the sequence of each antisense polynucleotide, and a schematic illustration comparing the design of each polynucleotide.

An experiment comparing the inhibition potency of a chimeric polynucleotide according to one embodiment of the invention with two conventional gapmer antisense oligonucleotide was conducted. The polynucleotide structures and the results of the experiment are shown in FIG. 7. The control gapmers are 13 bases (ApoB1 ASO 13mer; SEQ ID NO:6) and 20 bases (ApoB1 ASO 20mer-4; SEQ ID NO:2) in length. The 13mer control has a central region of 8 phosphorothioated DNA nucleotides, a first 5'-wing region of 2 LNA bases and a first 3'-wing region of 3 LNA bases, but does not have a second wing on either side. The 20mer control has the same structure as the 13mer, and adds 4 phosphorothioated 2'-O-Me RNA bases at the 5' end and 3 phosphorothioated 2'-O-Me RNA bases at the 3' end. According to the disclosure, these bases are not low protein-affinity nucleotides (because they are phosphorothioated) and thus they do not constitute a second 5' or 3'-wing region. They would actually be classified as part of the first wing region (and thus the 20mer control is a gapmer with a 6 base 5'-wing region and a 6 base 3'-wing region).

The chimeric polynucleotide ApoB1 ASO 20mer-5; SEQ ID NO:7) contains an 8 base central region, a first 5'-wing region of 2 LNA bases and a first 3'-wing region of 3 LNA bases, and adds to that a second 5'-wing region of 4 2'-O-Me RNA bases and a second 3'-wing region of 3 2'-O-Me RNA bases. The 2'-O-Me RNA bases are low protein-affinity nucleotides and thus constitute second wing regions.

The three ASO's were tested in vivo using Hep 1-6 liver cells according to the following procedure.

The ASOs were each transfected using Lipofectamine 2000 (manufactured by Invitrogen, Inc.) according to the usage protocol provided with the reagent. The concentration of each ASO in the medium at the time of the transfection was 2 nM, 10 nM, and 20 nM. Furthermore, controls having no ASO added to the cells were also prepared. Subsequently, 24 hours after the transfection, the cells were collected by using Isogen, and mRNA's were collected according to the manufacturer's usage protocol and the amount of mRNA was determined.

cDNA's were synthesized from certain amounts of the mRNA's by using SuperScript III according to the manufacturer's protocol. Subsequently, the cDNA obtained was used as templates, and quantitative RT-PCR was carried out by using a TaqMan system. The primers used in the quantitative RT-PCR were those designed and produced by Life Technologies Corp. based on the various gene numbers. The PCR conditions for temperature and time were as follows: 15 seconds at 95° C., 30 seconds at 60° C., and 1 second at 72° C. were designated as one cycle, and 40 cycles thereof were carried out. Based on the results of the quantitative RT-PCR thus obtained, the amount of expression of rApoB/amount of expression of rGAPDH (internal standard gene) were respectively calculated, and the calculation results for the control group and the calculation results for the nucleic acid-administered groups were compared and evaluated by a t-test. The results thus obtained are presented in FIG. 7.

As shown by the results in FIG. 7, all three ASOs show an antisense effect, with greater inhibition obtained at higher concentration of the ASO. However, comparing the inhibition potency of the 20mer chimeric polynucleotide with the 20mer control, the chimeric polynucleotide provides a greater degree of inhibition. Although the potency of the 13mer control is still greater, the presence of the second wing provides improved performance compared to the convention 20mer control ASO, and is expected to have a reduced toxicity compared to the 13mer control. The result reveals that including a second wing region provides improved antisense performance.

Example 2

An experiment comparing the inhibition potency of a chimeric polynucleotide according to embodiments of the invention having either a second 5'-wing region, a second 3'-wing region, or both wing regions was conducted. The polynucleotide structures and the results of the experiment are shown in FIG. 8A. Two conventional gapmer controls were compared with the inhibition potency of 3 different chimeric polynucleotides.

Figure 8B:
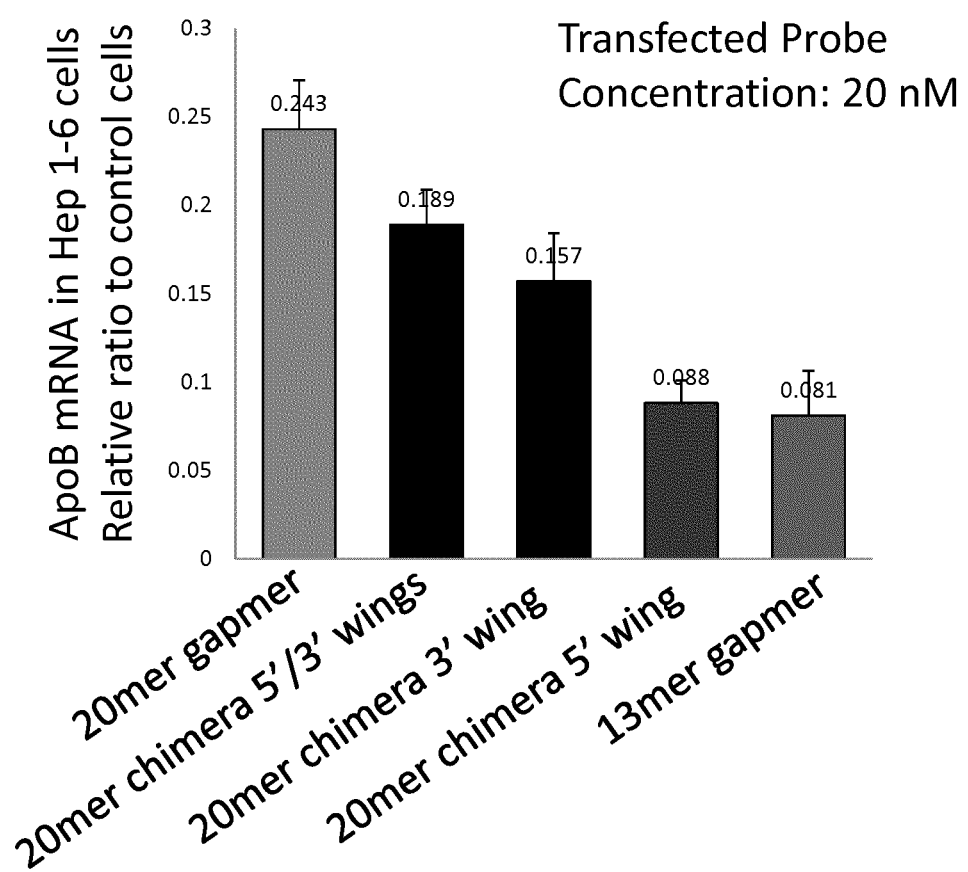
FIG. 8B shows a graph illustrating the results obtained upon administering to Hep 1-6 cells "20mer gapmer," "20mer chimera 5'/3' wings," "20mer chimera 3' wing," "20mer chimera 5' wing," and "13mer gapmer," all of which have a sequence complementary to the base sequence of ApoB1 gene, and analyzing the amount of expression of ApoB1 gene in the cells by quantitative PCR.

The ASO's were tested in vivo using Hep 1-6 liver cells according to the procedure described in Example 1, and the results are shown in FIG. 8B. The ASOs were transfected at a concentration of 20 nM.

As shown by the results in FIG. 8B, all five ASOs show an antisense effect relative to the negative control (no ASO). However, comparing the inhibition potency of the 20mer chimeric polynucleotides with the 20mer control, the chimeric polynucleotide provides a greater degree of inhibition in all three cases. Significantly, the chimeric polynucleotide with a second 5'-wing demonstrated a potency that is statistically the same as the inhibition achieved with the 13mer control. Thus, the presence of the second wing yields a performance with a 20mer ASO that is the same as that obtained with a 13mer gapmer. Moreover, the 20mer chimeric polynucleotide is expected to have a reduced toxicity compared to the 13mer control.

Example 3

Next, the chimeric polynucleotides were tested in vivo in mice. The sequences and design of the ASO probes and controls are shown in FIG. 9. The ASO were intravenously injected to a mouse in an amount of 3.0 mg/kg each through the tail vein. The mice were 4-week old female ICR mice with body weights of 20 to 25 g. The experiments using mice were all carried out with n=3. Also, as a negative control group, mice to which only PBS was injected instead of the single-stranded ASO or double-stranded nucleic acid complex were also prepared. Seventy-two hours after the injection, the mice were perfused with PBS, and then the mice were dissected to extract the liver. Subsequently, extraction of mRNA, synthesis of cDNA, and quantitative RT-PCR were carried out by the same methods as the methods described in Example 1, the amount of expression of mApoB/amount of expression of mGAPDH (internal standard gene) was calculated, and comparisons were made between the group administered with PBS (PBS only) and the groups administered with a nucleic acid. The results thus obtained are presented in FIG. 9.

As illustrated in FIG. 9, two ASOs show an antisense effect (13mer control and the 20mer-5 chimeric polynucleotide), but the two 20mer controls (20mer-1 and 20mer-4), do not show an antisense effect. Although the potency of the 13mer control is still greater than the chimeric polynucleotide, the presence of the second wing provides improved performance compared to the convention 20mer control ASOs, and is expected to have a reduced toxicity compared to the 13mer control. The result reveals that including a second wing region provides improved antisense performance in vivo.

Example 4

Design and synthesis of Toc(tocopherol)-HDO. A series of DNA-LNA gapmers or chimeramers of different lengths (13- to 23-mers) were designed to target mouse ApoB mRNA (NM_009693), and were synthesized by Gene Design (Osaka, Japan) and Hokkaido System Science (Sapporo, Japan). The sequences of the chimeramers targeting ApoB mRNA were as follows:

1) ApoB1 13mer,
(SEQ ID NO: 1)
5'-G(L)^C(L)^a^t^t^g^g^t^a^t^T(L)^C(L)^A(L)-3';

2) ApoB1 Toc13mer PS(-),
(SEQ ID NO: 1)
5'-Toc_G(L)^C(L)^a^t^t^g^g^t^a^t^T(L)^C(L)^A(L)-3';

3) ApoB1 Toc17merPS(-),
(SEQ ID NO: 2)
5'-Toc-U(X)-C(X)-C(X)-A(X)-
G(L)^C(L)^a^t^t^g^g^t^a^t^T(L)^C(L)^A(L)-3,;

4) ApoB1 Toc20merPS(-),
(SEQ ID NO: 3)
5'-Toc-A(X)-A(X)-G(X)-U(X)-C(X)-C(X)-A(X)-G(L)^C
(L)^a^t^t^g^g^t^a^t^T(L)^C(L)^A(L)-3,;

```
5) ApoB1 Toc20merPS(+)
                                              (SEQ ID NO: 4)
5'-
Toc^A(X)^A(X)^G(X)^U(X)^C(X)^C(X)^A(X)^G(L)^C(L)
^a^t^
t^g^g^t^a^t^T(L)^C(L)^A(L)-3';
and 6) ApoB1 TocPEG13mer
                                              (SEQ ID NO: 1)
5'-Toc^spacer18^G(L)^C(L)^a^t^t^g^g^t^a^t^T(L)^C-
(L)^A(L)3';
``` wherein lower case represent DNA, upper case with L be noted in brackets represent LNA (capital C denotes LNA methylcytosine), upper case with X be noted in brackets represent UNA or 2'-O-methyl sugar modification, chevron mark represent phosphorothioate linkages.

Mouse Studies.

Wild type Crlj:CD1 (ICR) mice aged 4-5 weeks (Oriental Yeast, Tokyo, Japan) were kept on a 12-h light/dark cycle in a pathogen-free animal facility with free access to food and water. ASO gapmer or chimeramer was administered to the mice by tail vein injection based upon body weight. All oligonucleotides were formulated in PBS, which was also used as the control. The oligonucleotides were administered to wild-type mice by a single injection of 0.75-6 mg/kg. For postmortem analyses, mice were deeply anesthetized first with intraperitoneally administered 60 mg/kg pentobarbital, and then sacrificed by transcardiac perfusion with PBS after confirming the absence of blink reflex. All animal experiments were performed in accordance with the ethical and safety guidelines for animal experiments of Tokyo Medical and Dental University (#0140144A).

Quantitative Real-Time Polymerase Chain Reaction Assay.

Total RNA was extracted from mouse liver by using Isogen (Nippon Gene, Tokyo, Japan). To detect mRNA, DNase-treated RNA (2 µg) was reverse transcribed with SuperScript III and Random Hexamers (Life Technologies, Carlsbad, Calif.). To detect RNAs, quantitative real-time polymerase chain reaction (RT-PCR) analysis was performed by using the Light Cycler 480 Real-Time PCR Instrument (Roche Diagnostics, Mannheim, Germany). The primers and probes for mouse ApoB, glyceraldehyde-3-phosphate dehydrogenase (Gapdh; NM_008084) genes were designed by Applied Biosystems. The results thus obtained are presented in FIG.

Figure 10:
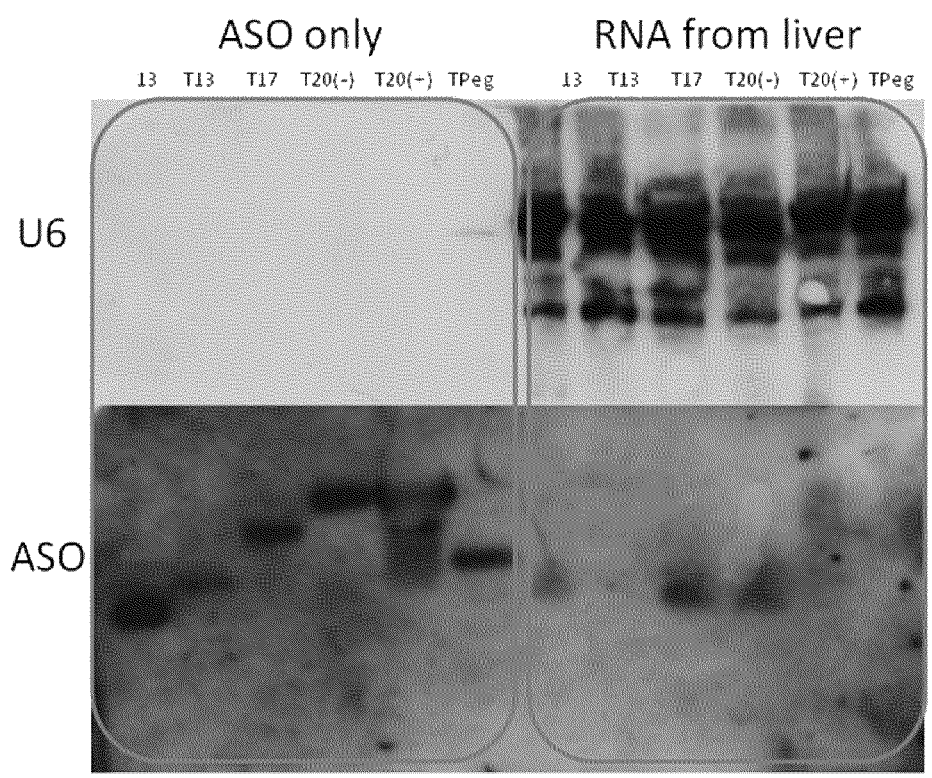
FIG. 10 shows a result of Northern blot analysis. The hybridized signals of T17 and T20(-) missing in liver to length of 13mer were detected (lower right panel) The mouse U6 (internal control) is shown in upper panel.

Northern blot analysis. Total RNA was extracted from mouse liver by using Isogen II (Nippon Gene). Total RNA (45 µg) was separated by electrophoresis in an 18% polyacrylamide-urea gel and transferred to a Hybond-N+ membrane (Amersham Biosciences, Piscataway, N.J.). The blot was hybridized with a probe corresponding to the cRNA sequence, or with the mouse U6 micro RNA sequence (internal control), which had been labeled with digoxigenin-ddUTP by using a DIG Oligonucleotide 3'-End Labelling Kit, 2nd Generation (Roche Diagnostics). The sequence of the DNA probe for detecting gapmer or chimeramer was 5'-TGAATACCAATGCTG-3' (SEQ ID NO:19). The signals were visualized by Gene Images CDP-star Detection Kit (Amersham Biosciences). The results thus obtained are presented in FIG. 10.

Figure 11:
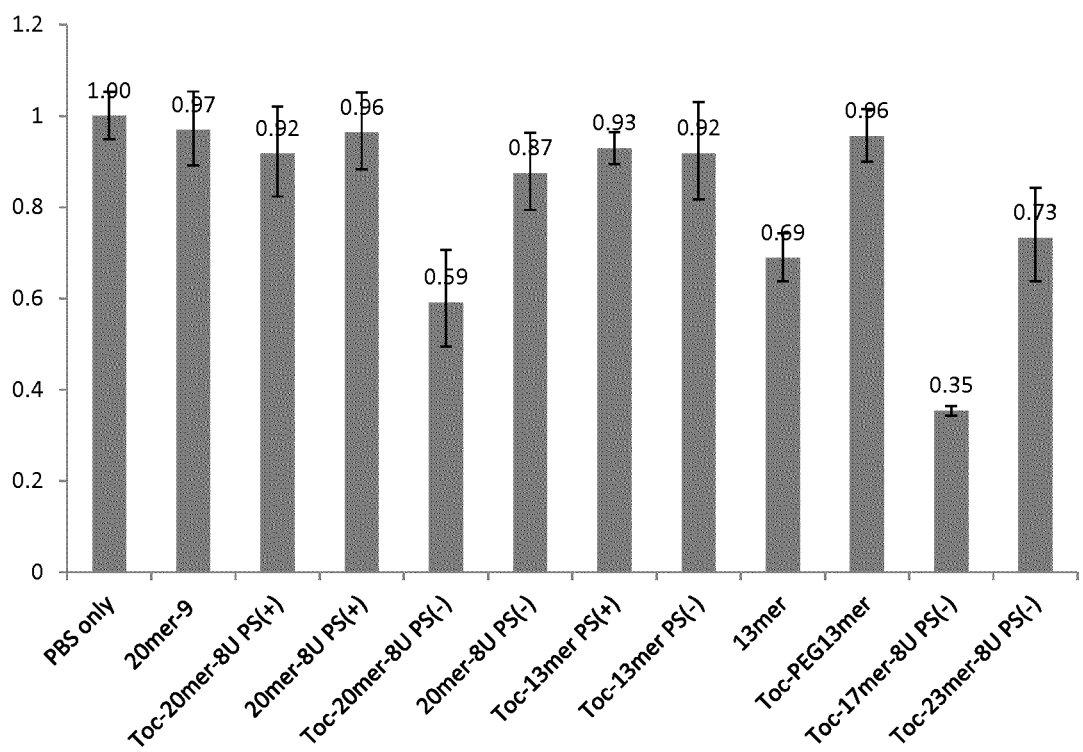
FIG. 11 illustrates relative antisense effect of various chimeric single-stranded polynucleotides.
Figure 12:
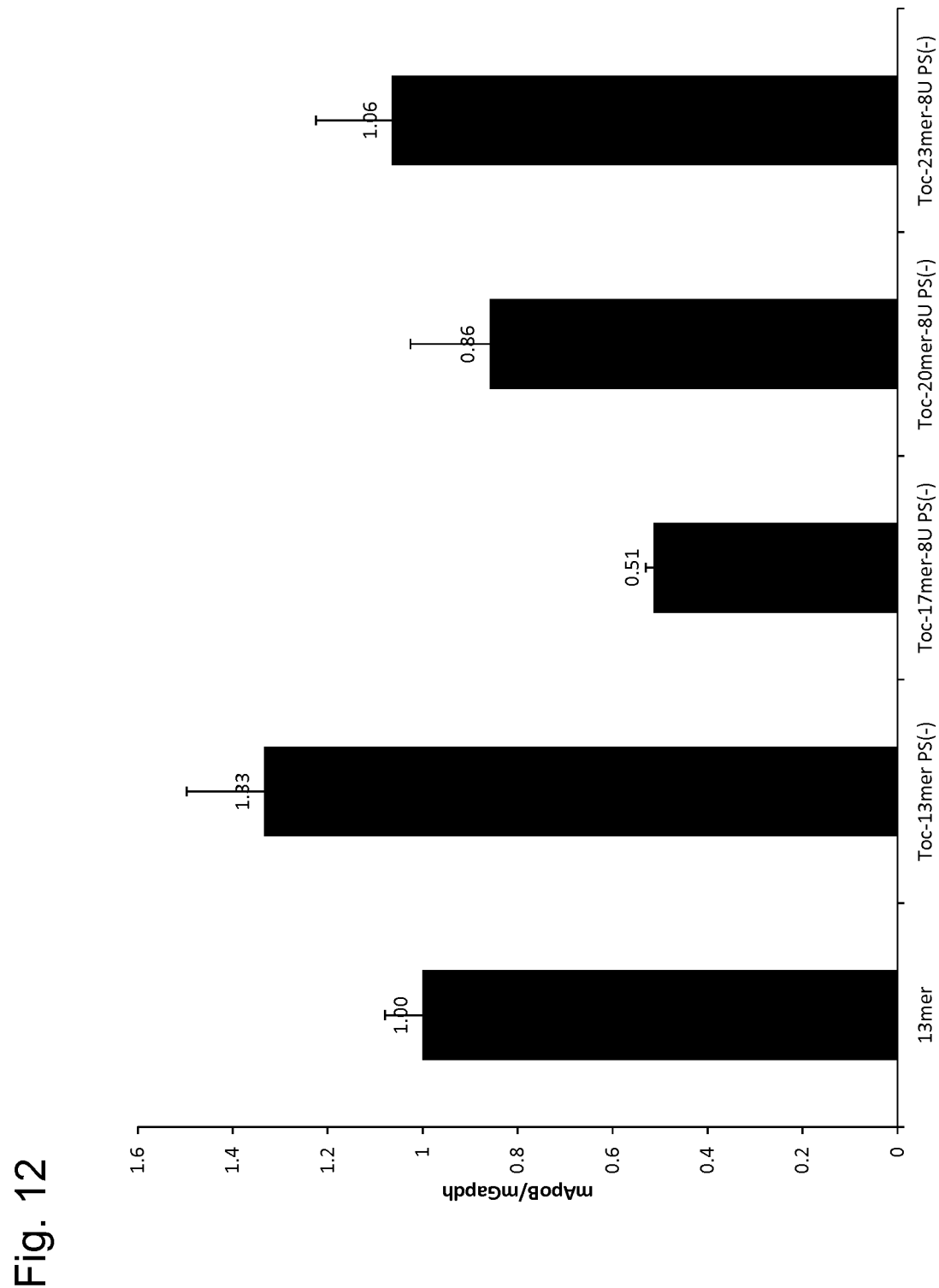
FIG. 12 indicates ApoB mRNA expression level normalized by Gapdh mRNA expression level compared to control 13mer.
Figure 13:
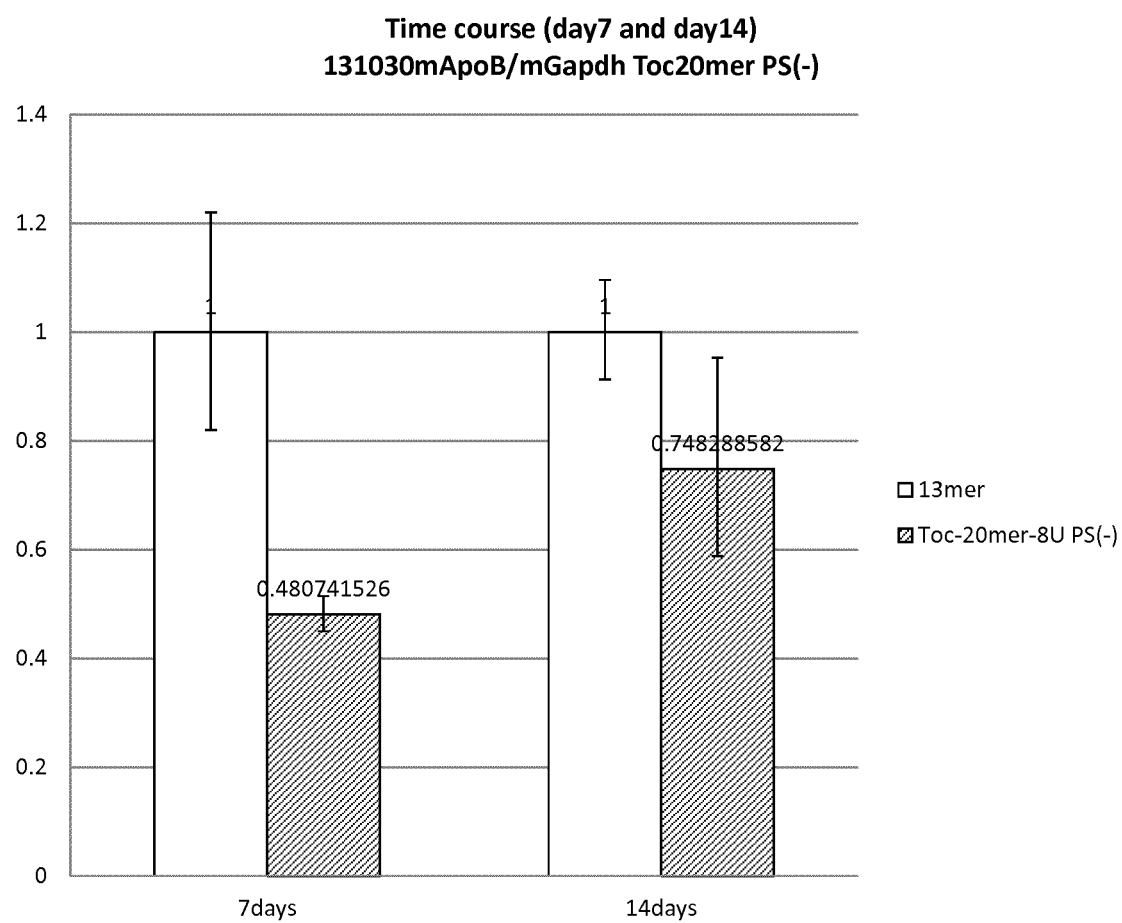
FIG. 13 shows comparison or time course of antisense effect of 13mer and Toc-20mer-8U PS(-) single-stranded polynucleotides.
Figure 14:
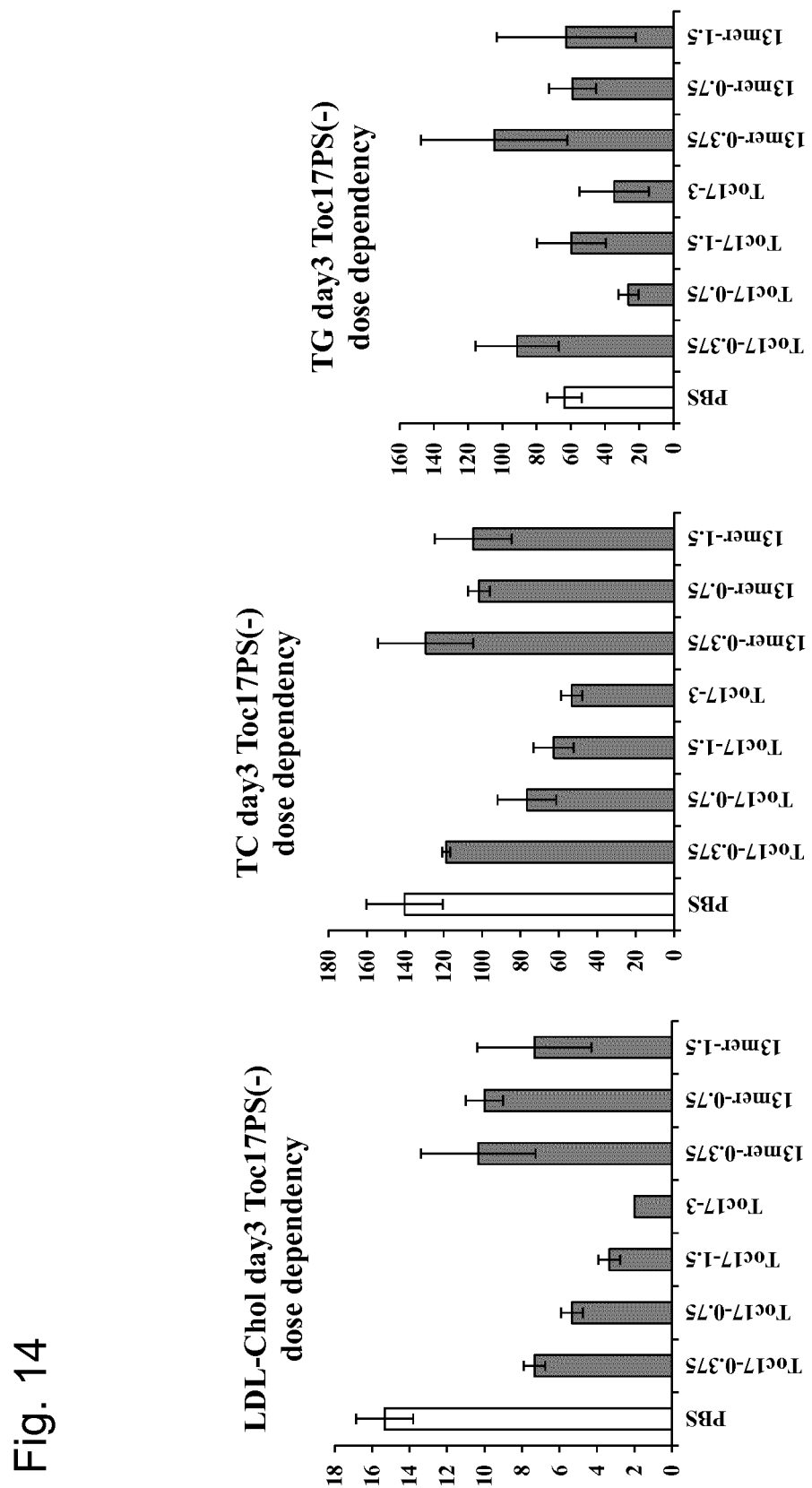
FIG. 14 indicates effect of various chimeric single-stranded polynucleotides on lipid level (LDL-Cholesterol, total cholesterol and triglyceride).

As illustrated in FIG. 11 and FIG. 12, three ASOs (the 13mer control the Toc-17-mer-8U PS– and the Toc-20-mer-8U PS– chimeric polynucleotide) show an antisense effect. On the other hand, the two 20mer controls (20mer-9 and 20-mer-8U PS+), do not show an antisense effect. The potency of the Toc-20-mer-8U PS– is still greater than those of the other two chimeric polynucleotide (the 13mer control and Toc-20-mer-8U PS– chimeric polynucleotide). Moreover, the efficacy of the Toc-20-mer-8U PS– prolonged up to 14 days after injection (FIG. 13). Furthermore, the potency of the Toc-20-mer-8U PS– was dose dependent manner (FIG. 14). These results suggest that the presence of the second wing having no PS provides improved performance compared to the convention 20mer control ASOs with PS and the set forth above 20-mer-8U PS-ASO is expected to have a reduced toxicity compared to control.

A "high-exonuclease resistant nucleotide" is a nucleotide that is (i) more resistant to DNase or RNase than a natural DNA or RNA nucleotide, (ii) more resistant to exonuclease than a natural DNA or RNA nucleotide and (III) relatively same or lower resistant to endonuclease than a natural DNA or RNA nucleotide.

Examples of high-exonuclease resistant nucleotides include 2'-O-methyl RNA nucleotides, 2'-O-methoxyethyl RNA nucleotides, LNA, cMOE BNA, 2-fluoro RNA nucleotides, boranophosphate nucleotides, methylphosphonate nucleotides, phosphoramidite nucleotides, 5-methylcytosine, 5-propynyluridine, and unlocked nucleic acid (UNA).

Example 5

Next, a double-stranded antisense agent was tested in vivo in mice. The sequences and design of the various antisense probes and the complementary strands are shown in FIG. 16A. In the complementary strands, tocopherol (Toc) was bound to the 5' terminus. Thus, a functional moiety capable of directing the delivery of the double-stranded agent, and presumably the chimeric antisense polynucleotide, to the liver was incorporated in the complementary strand.

The binding of the tocopherol moiety to the cRNA was carried out according to a known technique, by preparing tocopherol amidite in which the hydroxyl group at the 6-position of the chromane ring of tocopherol was joined to the phosphoramidite, and then the tocopherol amidite was coupled to the 5'-terminus of the RNA by standard coupling methods.

The sequence, composition, and strand length of the antisense polynucleotides and the complementary strands (cRNA) were as follows:

Antisense Strands

```
1. 20mer-1 ApoB1 ASO:
                                              (SEQ ID NO: 5)
5'-T_sC_sC_sA_sG_sC_sa_st_st_sg_sg_st_sa_st_sT_sC_sA_sG_sT_sG-3'

2. 20mer-4 ApoB1 ASO:
                                              (SEQ ID NO: 6)
5'-u_sc_sc_sa_sG_sC_sa_st_st_sg_sg_st_sa_st_sT_sC_sA_sg_su_sg-3'

3. 20mer-5 ApoB1 ASO:
                                              (SEQ ID NO: 7)
5'-uccaG_sC_sa_st_sg_sg_st_sa_st_sT_sC_sAgug-3'

4. 13mer ApoB1 ASO:
                                              (SEQ ID NO: 8)
5'-G_sC_sa_st_st_sg_sg_st_sa_st_sT_sC_sA-3'
```

(Upper case: LNA; lower case: DNA; underlined: 2'-O-Me RNA; s: phosphorothioate between the bases)

Complementary Strands

```
1. 20-mer Toc-ApoB1 cRNA:
                                         (SEQ ID NO: 9)
   5'-Toc-c,a,c,u,g,AAUACCAAUG,c,u,g,g,a-3'

2. 13-mer Toc-ApoB1 cRNA:
                                         (SEQ ID NO: 10)
   5'-Toc-u,g,a,AUACCAAU,g,c-3'
```

(Upper case: RNA, underlined: 2'-OMe-RNA, s: phosphorothioate between the bases)

The antisense polynucleotides and the respective cRNA having the same length were mixed in equimolar amounts, and the mixtures were heated at 95° C. for 5 minutes and then were kept warm at 37° C. for one hour to thereby anneal these nucleic acid strands and form double-stranded nucleic acid complexes. The annealed nucleic acids were stored at 4° C. or on ice.

The double-stranded complexes were intravenously injected to a mouse in an amount of 0.75 mg/kg each through the tail vein. The mice were 4-week old female ICR mice with body weights of 20 to 25 g. The experiments using mice were all carried out with n=3. Also, as a negative control group, mice to which only PBS was injected instead of the double-stranded complexes were also prepared. Seventy-two hours after the injection, the mice were perfused with PBS, and then the mice were dissected to extract the liver. Subsequently, extraction of mRNA, synthesis of cDNA, and quantitative RT-PCR were carried out by the same methods as the methods described in Example 1, the amount of expression of mApoB/amount of expression of mGAPDH (internal standard gene) was calculated, and comparisons were made between the group administered with PBS (PBS only) and the groups administered with a nucleic acid. The results thus obtained are presented in FIG. 16B.

Figure 16B:
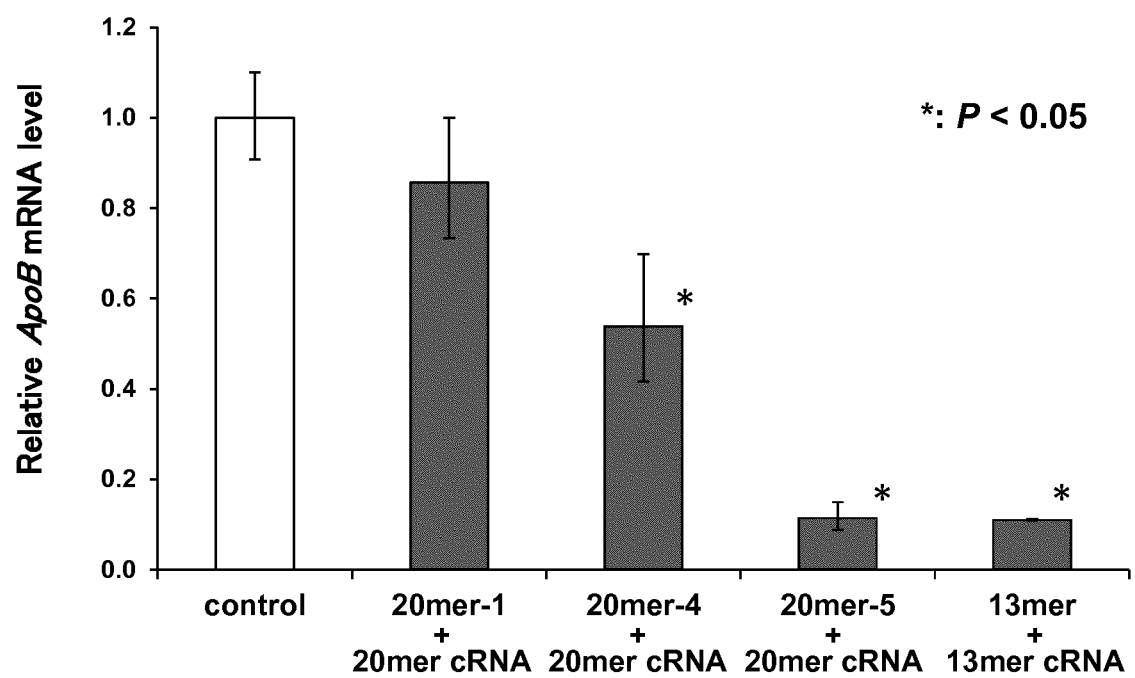
FIG. 16B is a graph illustrating the results obtained by administering the double-stranded complexes shown in FIG. 16A, to mice, and analyzing the amounts of expression of ApoB1 gene, whose transcription product is targeted by the antisense strand, in the mice.

As illustrated in FIG. 16B, three of the double-stranded complexes, those containing 20mer-4, 20mer-5, and 13mer ASOs showed a statistically significant level of suppression compared to the PBS control. Furthermore, the double-stranded agent comprising 20mer-5 ASO shows an antisense effect that is similar to that of the double-stranded 13mer gapmer control. Thus, the double wing structure in the 20mer-5 ASO provides improved performance compared to the conventional 20mer control ASOs, and is expected to have a reduced toxicity compared to the 13mer control. The result demonstrates that double-stranded antisense agents that comprise a chimeric antisense polynucleotide (i.e., an antisense polynucleotide having a double wing structure, in this instance, and second wing on both the 3' and 5' ends of the polynucleotide) provides improved antisense performance in vivo.

We claim:

1. A double-stranded antisense agent comprising the following chimeric antisense polynucleotide and a complementary strand annealed to the chimeric antisense polynucleotide:
   a chimeric antisense polynucleotide comprising:
      a center nucleotide region comprising at least 5 nucleotides;
      a first 5'-wing region joined to the 5' end of the center nucleotide region consisting of 2-5 nucleotides wherein at least 1 is a nucleotide analog;
      a first 3'-wing region joined to the 3' end of the center nucleotide region consisting of 2-5 nucleotides wherein at least 1 is a nucleotide analog; and
      a second 5'-wing region and/or a second 3'-wing region, wherein:
      the second 5'-wing region is joined to the 5' end of the first 5'-wing region and consists of 7 nucleotides which are 2'-O-methyl RNA nucleotides or UNA, which are not phosphorothioated; and
      the second 3'-wing region is joined to the 3' end of the first 3'-wing region and consists of 7 nucleotides which are 2'-O-methyl RNA nucleotides or UNA, which are not phosphorothioated;
      wherein the nucleotides in the first wing regions are bridged nucleotides; and
   wherein the total number of nucleotides, nucleotide analogs, and 2'-O-methyl RNA nucleotides or UNA of the chimeric antisense polynucleotide is no more than 35 nucleotides, the center nucleotide region comprises nucleotides that (i) are independently selected from DNA and phosphorothioate DNA nucleotides and (ii) hybridize to an RNA polynucleotide, the total length of which is no more than 35 nucleotides, to form a duplex that is recognized by RNase H.

2. The double-stranded antisense agent of claim 1, wherein at least one of the nucleotides in the center nucleotide region is phosphorothioated.

3. The double-stranded antisense agent of claim 2, wherein all nucleotides in the center nucleotide region are phosphorothioated.

4. The double-stranded antisense agent of claim 1, wherein the bridged nucleotides are independently selected from LNA, cEt BNA, amideBNA, and cMOE BNA.

5. The double-stranded antisense agent of claim 1, wherein at least one of the nucleotide analogs in the center nucleotide region and the first wing region(s) are phosphorothioated.

6. The double-stranded antisense agent of claim 1, wherein the chimeric antisense polynucleotide includes the second 5'-wing region.

7. The double-stranded antisense agent of claim 1, wherein the chimeric antisense polynucleotide includes the second 3'-wing region.

8. The double-stranded antisense agent of claim 1, wherein the chimeric antisense polynucleotide includes the second 5'-wing region and the second 3'-wing region.

9. The double-stranded antisense agent of claim 1, wherein the chimeric antisense polynucleotide further comprises a functional moiety joined to the 3'-end and/or the 5'-end of the chimeric antisense polynucleotide.

10. The double-stranded antisense agent of claim 9, wherein the functional moiety has a function selected from a labeling function, a purification function, and a targeted delivery function.

11. The double-stranded antisense agent of claim 9, wherein the functional moiety is joined to the chimeric antisense polynucleotide via a cleavable linker moiety.

12. The double-stranded antisense agent of claim 9, wherein the functional moiety is a molecule selected from a lipid, a peptide, and a protein.

13. The double-stranded antisense agent of claim 1, wherein the chimeric antisense polynucleotide can hybridize to a cellular transcription product in a 100 mM sodium chloride, 10 mM sodium phosphate buffer, pH 7.2, at 25° C.

14. The double-stranded antisense agent of claim 13, wherein the center region is fully complementary to the cellular transcription product to which the chimeric antisense polynucleotide can hybridize.

15. The double-stranded antisense agent comprising the chimeric antisense polynucleotide of claim 1, wherein the complementary strand further comprises a functional moiety joined to the 3'-end and/or the 5'-end.

16. The double-stranded antisense agent of claim 15, wherein the functional moiety has a function independently selected from a labeling function, a purification function, and a targeted delivery function.

17. The double-stranded antisense agent of claim 15, wherein the functional moiety is independently joined to the chimeric antisense polynucleotide and/or the complementary strand via a cleavable linker moiety.

18. The double-stranded antisense agent of claim 15, wherein the functional moiety is a molecule independently selected from a lipid, a peptide, and a protein.

19. A pharmaceutical composition comprising the double-stranded antisense agent of claim 1, and a pharmaceutically acceptable carrier.

20. The chimeric antisense polynucleotide of claim 1, wherein the second 5'-wing region and/or the second 3'-wing region comprise at least one mismatched base when the chimeric antisense polynucleotide hybridizes to the cellular transcription product to which the chimeric antisense polynucleotide can hybridize.

* * * * *